(12) United States Patent
Radojicic

(10) Patent No.: US 10,695,484 B1
(45) Date of Patent: Jun. 30, 2020

(54) SYSTEMS AND METHODS FOR LUMBAR CEREBROSPINAL FLUID ACCESS AND TREATMENT

(71) Applicant: AGATHOS HOLDINGS LLC, Lewes, DE (US)

(72) Inventor: Milan Radojicic, Los Gatos, CA (US)

(*) Notice: Subject to any disclaimer, the term of this patent is extended or adjusted under 35 U.S.C. 154(b) by 0 days.

(21) Appl. No.: 16/673,036

(22) Filed: Nov. 4, 2019

Related U.S. Application Data

(63) Continuation-in-part of application No. 12/857,555, filed on Aug. 16, 2010, now Pat. No. 10,478,555,
(Continued)

(51) Int. Cl.
*A61M 5/142* (2006.01)
*A61M 27/00* (2006.01)
(Continued)

(52) U.S. Cl.
CPC .... *A61M 5/14276* (2013.01); *A61M 5/14586* (2013.01); *A61M 25/04* (2013.01);
(Continued)

(58) Field of Classification Search
CPC ... A61B 5/032; A61B 5/14532; A61B 5/7214; A61M 2005/1726; A61M 2025/0002;
(Continued)

(56) References Cited

U.S. PATENT DOCUMENTS

| 5,429,582 | A | * | 7/1995 | Williams | ............ | A61M 25/1011 600/2 |
| 2003/0097082 | A1 | * | 5/2003 | Purdy | .............. | A61B 17/12136 600/594 |

(Continued)

OTHER PUBLICATIONS

Ommaya, A.K., "Implantable Devices for Chronic Access and Drug Delivery to the Central Nervous System", Cancer Drug Delivery 1(2) 1984, p. 169-179.
(Continued)

*Primary Examiner* — Brandy S Lee
(74) *Attorney, Agent, or Firm* — Stephen E. Zweig

(57) ABSTRACT

System and method for accessing and treating a patient's cerebrospinal fluid. The system comprises a device with at least one implantable single or multilumen catheter, configured for placement along a patent's cerebrospinal fluid pathway, with at least one domed subcutaneous reservoir and/or pump connected to the catheter(s). The device can also be equipped with control circuitry and controllable valves. The devices allow for drug administration and/or simultaneous, bidirectional cerebrospinal fluid access and exchange. The catheter(s), may be coupled with medical probes that transmit sensor data to the device's processor, which can be configured transmit and receive data and instructions. The catheters may also be configured with guide devices to facilitate implantation. Various configurations, from single dome to multiple dome devices are taught, along with various applications such as epidural and other cerebrospinal drug administration, and various medical diagnostic applications.

24 Claims, 15 Drawing Sheets

Related U.S. Application Data which is a continuation-in-part of application No. 12/228,697, filed on Aug. 16, 2008, now Pat. No. 9,770,180, which is a continuation-in-part of application No. 11/840,213, filed on Aug. 16, 2007, now abandoned.

(60) Provisional application No. 61/234,144, filed on Aug. 14, 2009, provisional application No. 60/822,640, filed on Aug. 17, 2006.

(51) Int. Cl.
| | | |
|---|---|---|
| *A61M 39/02* | (2006.01) | |
| *A61M 5/145* | (2006.01) | |
| *A61M 25/04* | (2006.01) | |
| *A61M 25/00* | (2006.01) | |

(52) U.S. Cl.
CPC ...... *A61M 27/006* (2013.01); *A61M 39/0208* (2013.01); *A61M 2005/14208* (2013.01); *A61M 2025/0007* (2013.01); *A61M 2039/0223* (2013.01); *A61M 2202/0464* (2013.01); *A61M 2210/1003* (2013.01)

(58) Field of Classification Search
CPC .. A61M 2025/0057; A61M 2210/1003; A61M 2230/201; A61M 25/00; A61M 27/006; A61M 39/0208; A61M 5/1428; A61M 5/1723
See application file for complete search history.

(56) References Cited

U.S. PATENT DOCUMENTS

| | | | | |
|---|---|---|---|---|
| 2006/0258970 | A1* | 11/2006 | Moskowitz | A61M 27/006 604/9 |
| 2009/0204019 | A1* | 8/2009 | Ginggen | A61M 27/006 600/561 |

OTHER PUBLICATIONS

Patwardhan, R.V., "Implanted ventricular shunts in the United States: The Billion-Dollar-A-Year Cost of the Hydrocephalus Treatment" Neurosurgery. 2005;56(1):139-44; discussion 144-5.

* cited by examiner

SYSTEMS AND METHODS FOR LUMBAR CEREBROSPINAL FLUID ACCESS AND TREATMENT

CROSS-REFERENCE TO RELATED APPLICATIONS

This application is a continuation in part of U.S. patent application Ser. No. 12/857,555, filed Aug. 16, 2010; application Ser. No. 12/857,555 was a continuation-in-part of U.S. patent application Ser. No. 12/228,697 filed on Aug. 16, 2008, now U.S. Pat. No. 9,770,180 issued Sep. 26; 2017; application Ser. No. 12/228,697 was a continuation in part of U.S. application Ser. No. 11/840,213 filed Aug. 16, 2007, now abandoned; application Ser. No. 11/840,213 claimed the priority benefit of U.S. provisional patent application 60/822,640, filed Aug. 17, 2006; application Ser. No. 12/857,555 also claimed the priority benefit of provisional patent application 61/234,144 filed Aug. 14, 2009; the entire contents of all of these applications are incorporated herein by reference.

BACKGROUND OF THE INVENTION

Field of the Invention

This is directed to systems and methods for cerebrospinal fluid access, analysis, treatment, diversion, and exchange.

Description of the Related Art

The cerebrospinal fluid is a window to the functioning of the central nervous system. In humans, approximately 500 ml/day of cerebrospinal fluid is produced. The CSF circulates and traverses the brain and spinal cord several times a day and exhibits a craniocaudal flow pattern influenced by the cardiac cycle.

The cerebrospinal fluid can provide both diagnostic and therapeutic opportunities for treating brain and spinal cord injury and disease. Disease and injury of the cerebrospinal fluid may manifest as alterations in the production or absorption of cerebrospinal fluid, alterations in cerebrospinal flow and dynamics and/or the accumulation of toxins, metabolites, and electrolytes in the fluid. Better diagnosis and therapeutics can, therefore, be achieved with systems and methods that improve the access, analysis, treatment, diversion, and exchange of the cerebrospinal fluid.

Seemingly disparate brain and spinal disorders may be connected by disruptions in the normal cerebrospinal fluid. Thus systems and methods the improve the access, analysis, treatment, diversion and exchange of the cerebrospinal fluid can better address central nervous trauma, hemorrhage, infections, toxins, metabolic derangements, structural malformations, cystic lesions, benign and malignant masses, imbalances of cerebrospinal fluid production and absorption and flow, neurodegenerative diseases, pain syndromes and neuropsychiatric disorders, pharmacological studies on the CNS and experimental studies of the C SF dynamics.

The problem of chronic access for therapeutics to the central nervous system has heretofore been limited to subcutaneous cranioventricular reservoirs. See, for example, the article "*Implantable Devices for Chronic Access and Drug Delivery to the Central Nervous System*" by Ommaya, *Cancer Drug Delivery* 1(2) 1984, p 169-179.

It has been noted that these subcutaneous cranioventricular reservoirs are prone to infection, are prone to obstruction by biological material and can migrate unintentionally into brain regions important for speech, motor or vision, thereby creating new morbidity and mortality. In many ways, cerebrospinal fluid shunts are prone to the same problems. These issues are discussed in the article "*Implanted ventricular shunts in the United States: The Billion-Dollar-A-Year Cost of the Hydrocephalus Treatment*" by Patwardhan et al., *Neurosurgery.* 2005; 56(1): 139-44; discussion 144-5.

BRIEF SUMMARY OF THE INVENTION

Prior art devices, such as the devices of Ommaya, had various problems. These include the problem that the placement of the prior art subcutaneous cranioventricular reservoir/pump devices of Ommaya requires general anesthesia which can be expensive.

Another problem with the prior art devices of Ommaya is that placement of this type of device requires a cranial burrhole and ventriculostomy procedure, which can be prone to complications and cosmetic concerns. Another problem is that the subcutaneous cranioventricular reservoir/pump also limits the volume of liquid that can be administered, due to the sensitive cranial cerebrospinal fluid dynamics that occur within the fixed skull space.

Other problems of prior art cranioventricular reservoir/pumps are that they only provide unidirectional flow of the cerebrospinal fluid, due to the single catheter and reservoir/pump design, meaning that fluid can only be withdrawn or infused at a time and never simultaneously. Such unidirectional flow can be desirable in certain situations because it can enable the use of simpler devices, but in other situations, greater flexibility is desirable.

The present invention is inspired, in part, by the insight that increasingly, cerebrospinal fluid will be utilized to diagnose and treat disease, including the filtering of toxins and metabolites. Unfortunately, the prior art devices such as Ommaya do not allow this. Furthermore, such prior art devices also lack any monitoring, reporting and/or control ability. Finally, placement of prior art subcutaneous cranioventricular reservoir/pumps necessitates repeating use of expensive imaging procedures, such as CT or MRI. This is problematic because, in addition to the high expense, repeat CT imaging can also increase patient radiation exposure, which is medically undesirable.

The present invention is thus inspired, in part, by the insight that what is needed are improved devices and methods that can provide a safer, faster, more flexible, and overall less expensive access to the cerebrospinal fluid for both purposes of drug administration and cerebrospinal fluid sampling. The invention thus teaches devices and methods with increased comprehensive diagnostic and therapeutic capability. These and other advantages of the present invention will become apparent from a consideration of the ensuing description and accompanying drawings.

In some embodiments, the present invention may be viewed as being a patient implantable device, system, or method for chronic access to a human patient's cerebrospinal fluid, that comprises at least one hollow catheter configured to access cerebrospinal fluid at one end, that is configured to transport fluid either to or from at least one fluid reservoir. Typically, this at least one reservoir will comprise a hollow dome configured to store fluid. This hollow dome comprises a substantially spheroidal cap with a cap-height and a substantially flat cap base with a cap base radius. Thus at least some forms of the hollow dome can act as a fluid reservoir.

Typically the substantially flat cap base(s) can be further mounted on a rigid support that is substantially parallel to the reservoir perimeter(s). Here "substantially" can mean within +/−20%.

Some embodiments of the hollow dome (reservoir dome, chamber, dome) may also comprise an elastic material configured to deform to a smaller deformed-cap-height in response to external pressure (such as from human fingers) applied to the reservoir, and then to elastically rebound to a higher cap-height when this external pressure is removed, thus creating a pumpable reservoir. This finger pressure pumping is occasionally referred to as "finger ballotment" or "priming with finger ballotment".

Thus, some embodiments of the dome or reservoir may further act as a reservoir and a pump, while other embodiments of the dome may act merely as a reservoir, and need not be configured with such elastic material. The term "reservoir/pump" is frequently used throughout this disclosure, somewhat interchangeably with "dome" and "chamber", with more specific meanings that can be determined from the local context.

Although Ommaya also taught a pumpable reservoir and a catheter, among other differences disclosed herein, the arrangement of the present invention's one or more catheters and tissue or bone attachment mechanisms are designed to overcome some of the disadvantages of Ommaya's device, such as the need to perform cranial burrhole and ventriculostomy procedures, as well as the distressing cosmetic aspects of mounting a device on the patient's head. This will be discussed in more detail later in this disclosure.

Thus the present invention is directed to devices and methods for chronically accessing the cerebrospinal fluid for diagnostics and therapeutics with an indwelling medical device. In some embodiments, this can be done by applying a lumbar intrathecal catheter tunneled to a subcutaneous dual, or at least one, reservoir/pump which can be accessed by an operator with needles. The subcutaneous dual, or at least one, reservoir/pump allows simultaneous, bidirectional cerebrospinal fluid access and flow and therefore cerebrospinal fluid exchange. Cerebrospinal fluid may be removed from the patient, or alternatively drugs or artificial cerebrospinal fluid may be administered to the patient by this mechanism. In multiple chamber configurations, the two or more chambers can be configured to prevent mixing, as desired. For simplicity, the multiple chamber embodiment is often referred by various two or dual-chamber (or dual dome) examples.

Although the single dome embodiments of the invention would, of course, be less functional than the multiple dome embodiments (e.g. dual dome), such single dome embodiments are not disclaimed, and indeed, due to their higher simplicity may be preferred in some situations.

In some of the multiple chamber or dome embodiments, two separate single lumen lumbar catheters, one for fluid inflow and another for fluid outflow, can be coupled to the subcutaneous dual reservoir/pump. In alternative embodiments, a single multilumen lumbar catheter can be coupled to the subcutaneous dual reservoir/pump.

In some embodiments, the subcutaneous dual, or at least one, reservoir/pump can be affixed by fasteners to the pelvis or other bone or tissue structures, and the device is again configured to accept the tunneled lumbar intrathecal catheter.

In some embodiments, the subcutaneous dual, or at least one, reservoir/pump is placed subcutaneously in the lower abdomen, and the device is configured to accept the tunneled lumbar intrathecal catheter.

In some embodiments, the lumbar catheter and subcutaneous dual reservoir/pump assembly may be coupled with other devices such as various external or subcutaneous drug pumps, cerebrospinal fluid pumps, anti-syphon technology, cerebrospinal fluid valves, cerebrospinal fluid dialyzers and/or filters.

In some embodiments, the lumbar catheter may be coupled to at least one medical probe or "sensor" connected to one or more wires within the catheter that transmit information (data) to I/O circuitry on the subcutaneous dual reservoir/pump. The medical probe can be configured to sense important physiological parameters.

In some embodiments, the catheter and subcutaneous dual reservoir/pump assembly can contain a computational device, such as a computer processor (e.g. processor integrated circuit chip) configured to compare actual physiological data with expected values stored in device memory.

In some embodiments, these physiological parameters are sent to communications circuitry on the reservoir/pump, allowing telemetric transmittal of key physiological variables and broadcasting an alert or warning signal to the patient or medical personnel.

In some embodiments, the communications circuitry of the reservoir/pump can be programmed by medical personnel with the telemetric transmittal of commands, not limited to changing opening valve pressures.

In some embodiments, the catheter and subcutaneous dual reservoir/pump assembly may have control circuitry and actuators that permit automatic interventions that bring the system toward homeostasis. Here, for example, the actuator may be a valve configured to regulate the flow of fluid, and the device may be configured to regulate a flow of fluid between the at least one catheter and the at least one reservoir.

Therefore, the subject invention results from a realization that a safer, lesser invasive, comprehensive and overall less expensive strategy for chronic access to the cerebrospinal fluid is effected by a lumbar intrathecal catheter tunneled to a subcutaneous reservoir/pump assembly comprising any of at least one reservoir, pump, and combination reservoir pump.

An algorithm may be programmed into a computational device and control circuitry on the reservoir/pump assembly, to identify an increasing rate of decease in the glucose concentration of the cerebrospinal fluid, and send a wireless warning signal to a patient or provider.

Figure 4A:
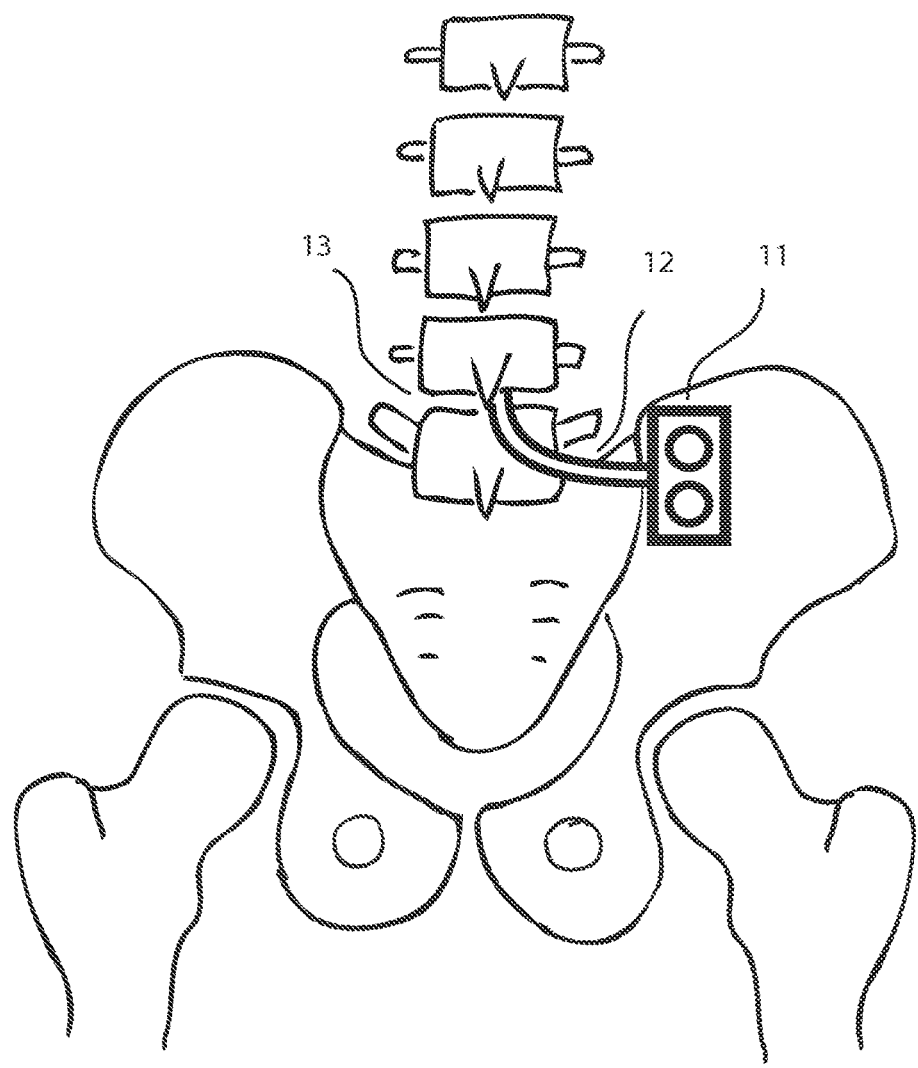

FIG. 4A shows the lumbar catheter and subcutaneous dual reservoir/pump fastened to the patient's posterior ilium. This area provides a convenient configuration for surgical implantation, tunneling, and chronic access.

Figure 4B:
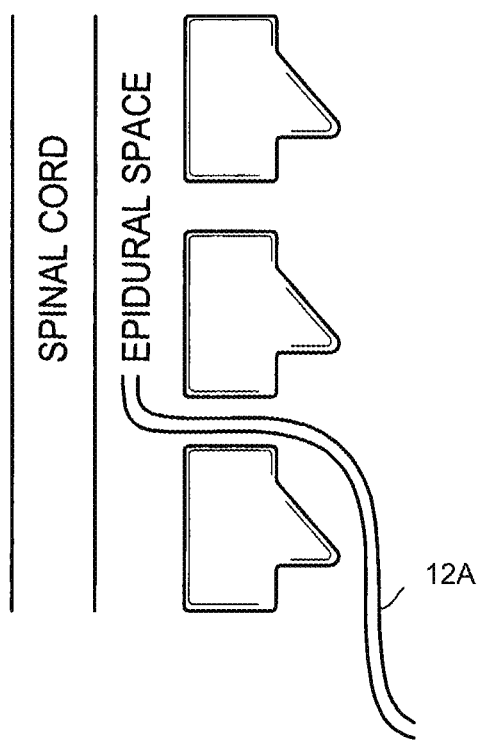

FIG. 4B shows an embodiment configured for spinal (epidural) applications, such as administering analgesics, other medication, or sampling the spinal cerebrospinal fluid in this area. This figure was taken from FIG. 5 of applicant's parent application Ser. No. 12/228,697 (now U.S. Pat. No. 9,770,180), the complete contents of which are incorporated herein by reference.

Figure 5A:
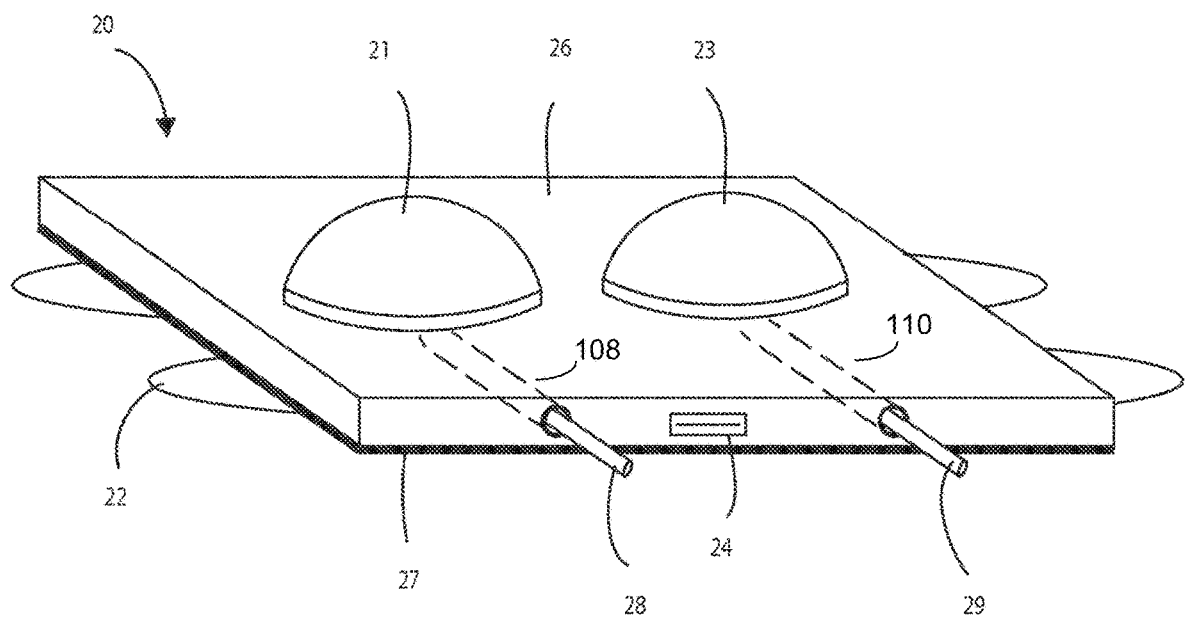

FIG. 5A shows the subcutaneous dual reservoir/pump. Two domes allow simultaneous inflow and outflow of fluid. Although the orientation of the domes may be vertical, horizontal or oblique, in a preferred embodiment, the base of the domes may be parallel to the base or support (27). The fluid "in" and "out" ports can be configured to differ in shape or consistency to alert a medical practitioner, who may be responsible for implanting the device, as to which port is "in" and which port is "out". A connector for the one or more wires transmitting data from the medical probe sensor, along with optional computational (processor) circuitry and wireless transmittal capability, may be housed in a needle impervious encasing, base, or support. Fasteners may be provided for affixing to an anatomic area, and the bottom (support or base) may be additionally reinforced to prevent the needle from passing through the device or any inline fluid conduits which allow the device to be connected in series or parallel with other devices.

Figure 5B:
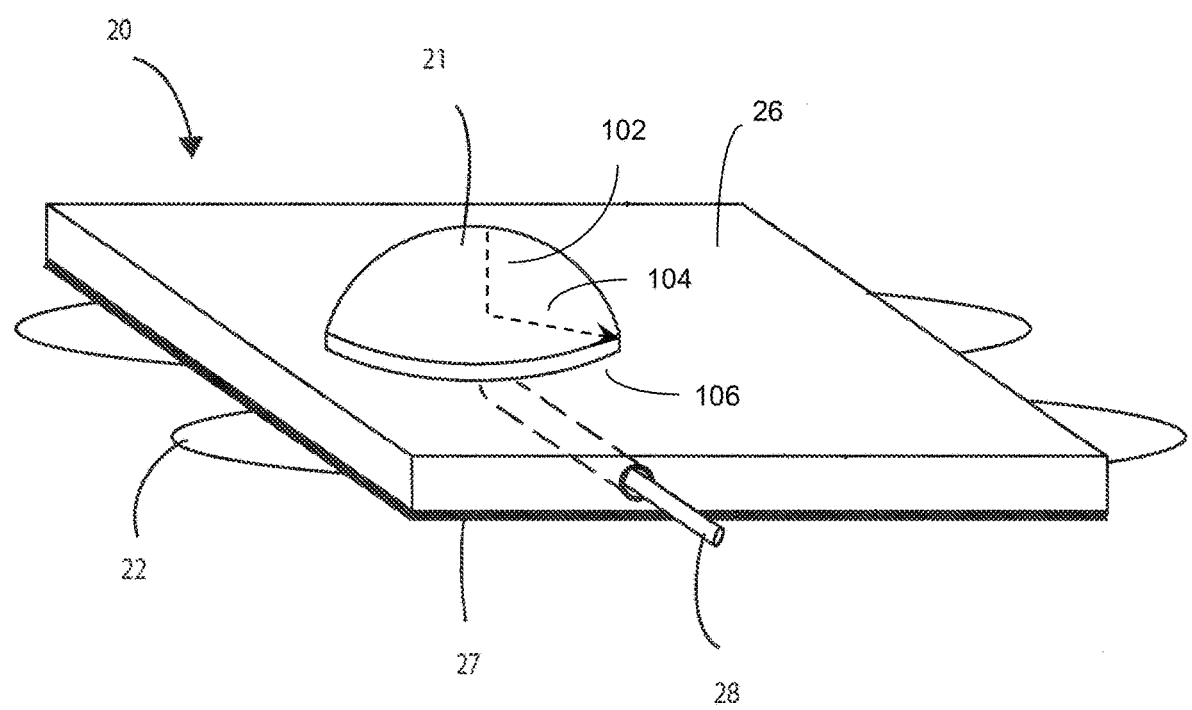

FIG. 5B shows an alternative embodiment of the subcutaneous reservoir/pump of FIG. 5A, here employing only a single dome. Here the dome is configured to function as at least a reservoir, but may not be configured to function as a pump.

Figure 5C:
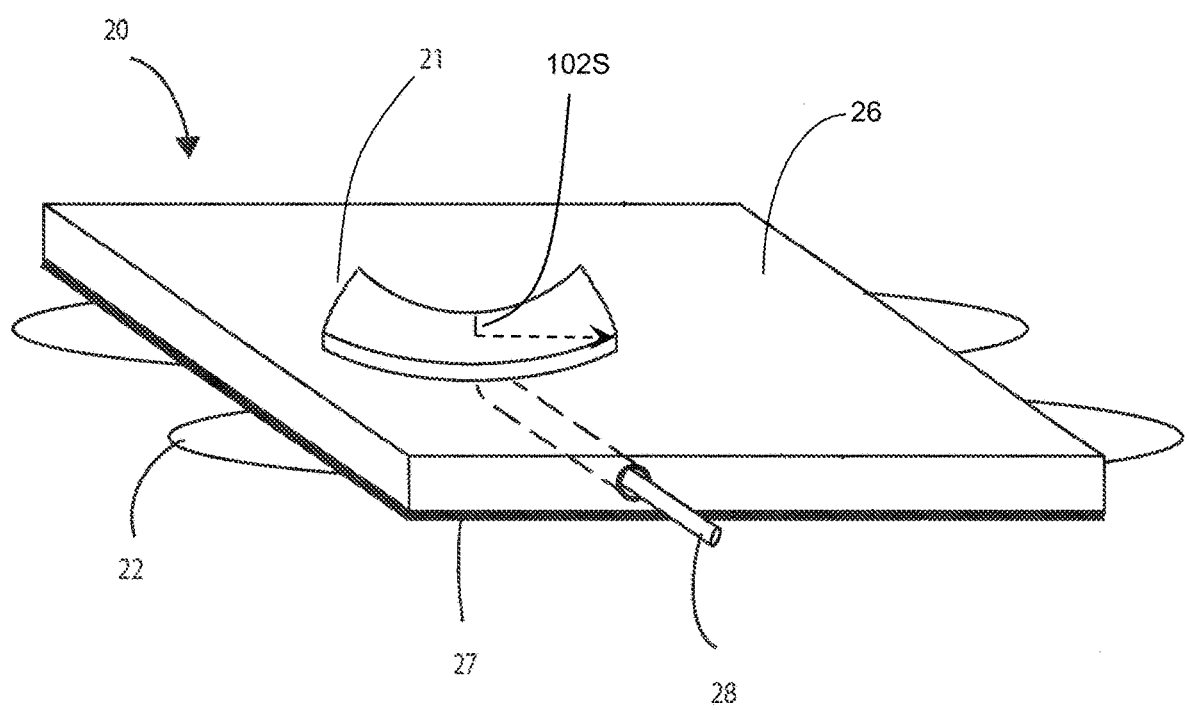

FIG. 5C shows an embodiment of the subcutaneous reservoir/pump in which the dome comprises an elastic material, and in which the dome also functions as a pump.

Figure 6:
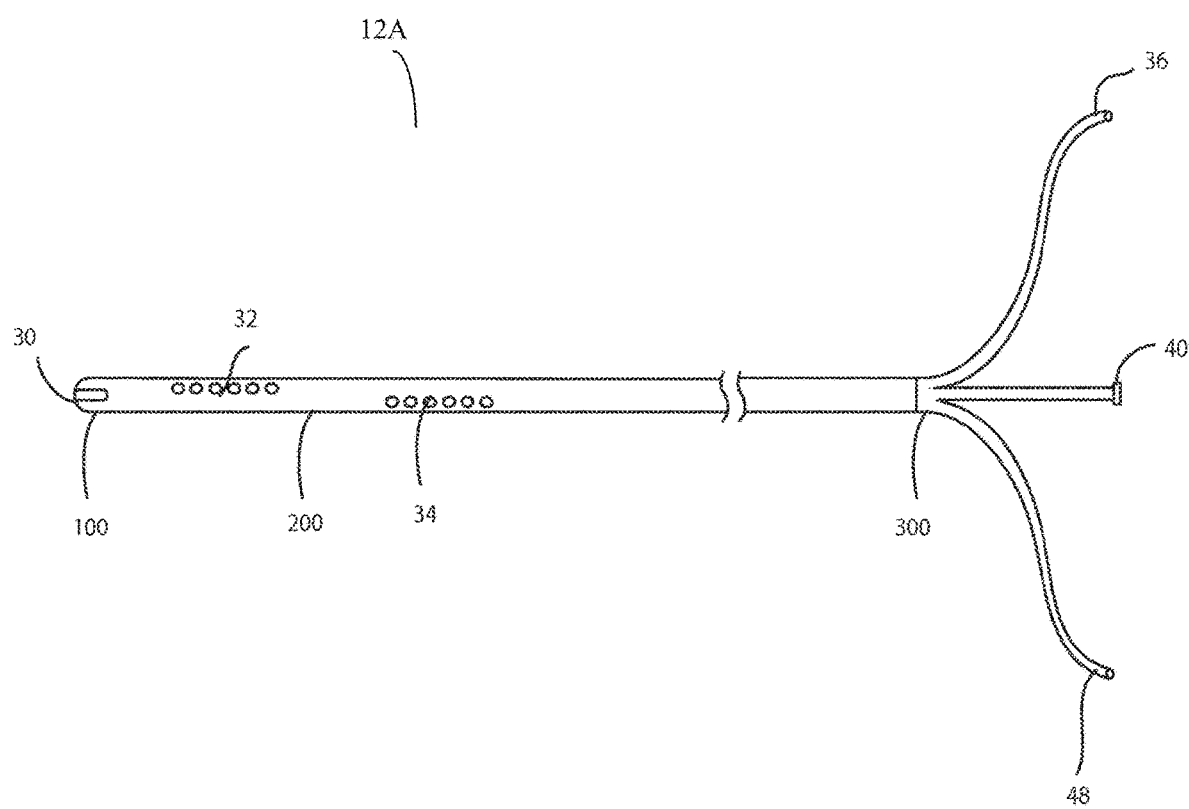

FIG. 6 shows the catheter, which may be a lumbar catheter, coupled with an optional medical probe. In some embodiments, the catheter may be a multilumen catheter configured for simultaneous inflow and outflow capabilities. The catheter may be made up of 3 sections: a distal 'work' section 100 (sometimes called the catheter distal end); an intermediate 'bulk fluid exchange' section 200 which is often either close to, or at, the catheter distal end; and a proximal 'connector' section 300, (e.g. catheter proximal end) usually configured to connect to the patient implantable device (20) either directly or via tubes, such as any of 36, 40, and 48.

Figure 7:
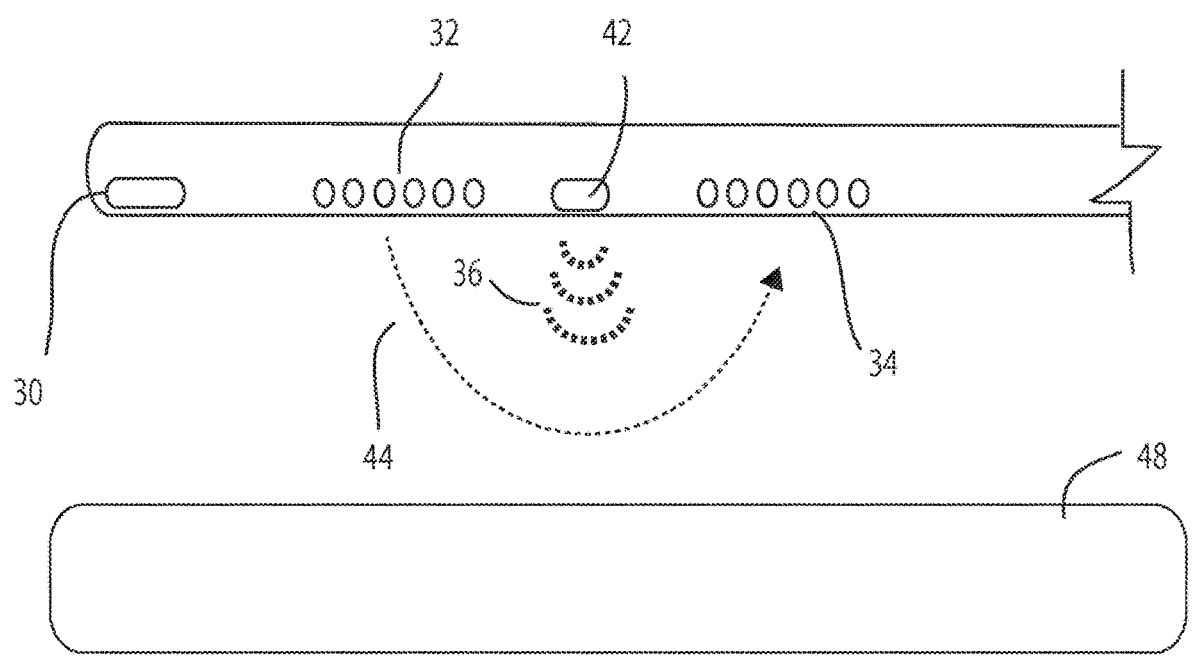

FIG. 7 shows the catheter with an optional medical probe at the tip. This medical probe can be used to navigate the catheter, sometimes in conjunction with a guidewire device, by forward-looking or side-fire linear orientation. In this example, The 'bulk fluid exchange' section 200 is fitted with 2 side fire fluid exchange sections, one for outflow and one for inflow. Between the fluid exchange sections is another medical instrument configured for transmitting or receiving energy. This configuration can be used for photoactivation of medications, cooling of tissue that may be heated by the medical instrument, or fluidic pulses to counteract negative pressure and microbubble formation by the medical instrument. Sensors that operate by transmitting or receiving energy may also be used.

Figure 8:
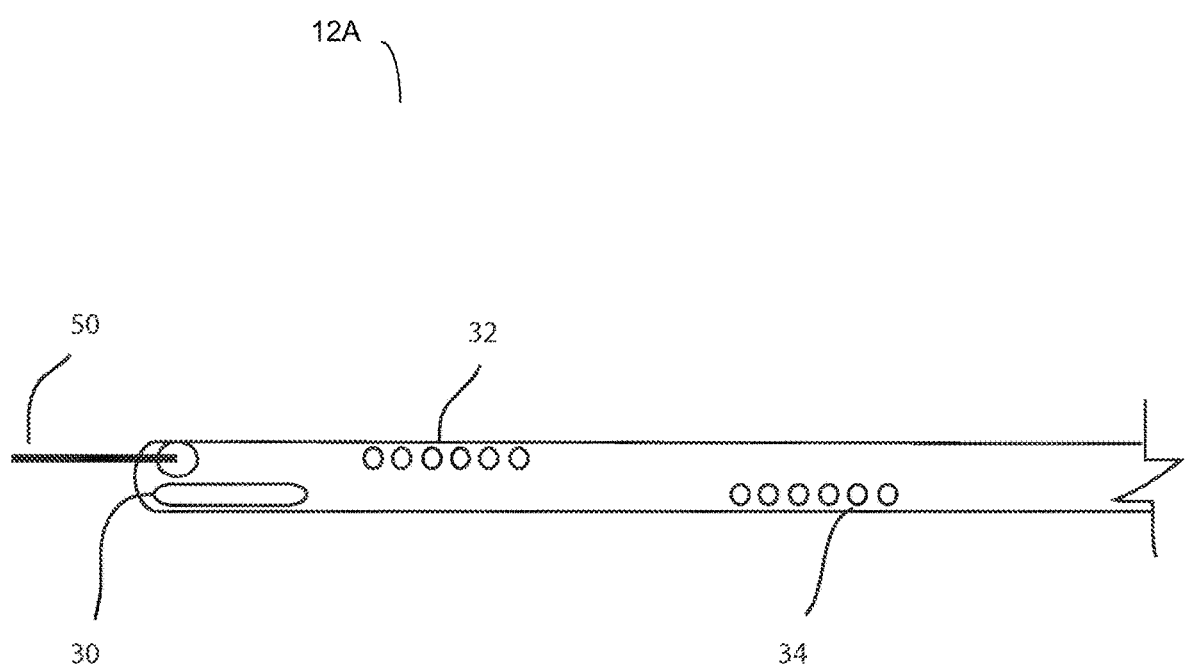

FIG. 8 shows the catheter coupled to an optional medical probe at the tip, with the addition of an endfire aperture and surgical tool conducting lumen. This surgical tool conducting lumen can be a hollow tube along the axis of a catheter, which may transmit a solid body (not limited to an electrical wire, guidewire or surgical tool), liquid or gas. This endfire aperture and lumen of the 'work' section can act as a sheath to introduce another surgical tool. In some embodiments, the medical probe(s) can be used to visualize the activity of the surgical tool.

Figure 9:
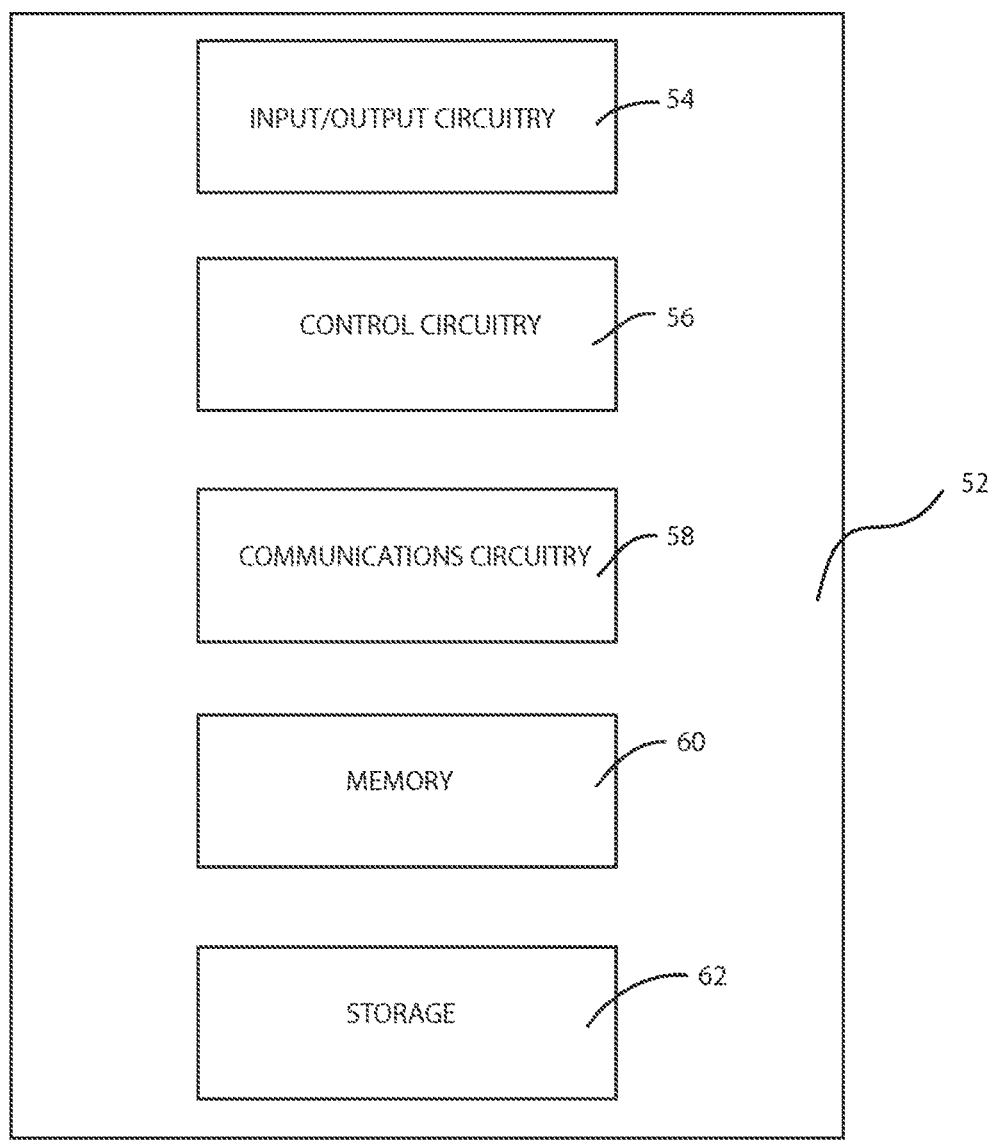

FIG. 9 shows the computational circuitry which can be coupled to or embedded on the subcutaneous dual reservoir/pump. The circuitry can be protected with a needle impervious and water-resistant sleeve material to prevent damage.

Figure 10:
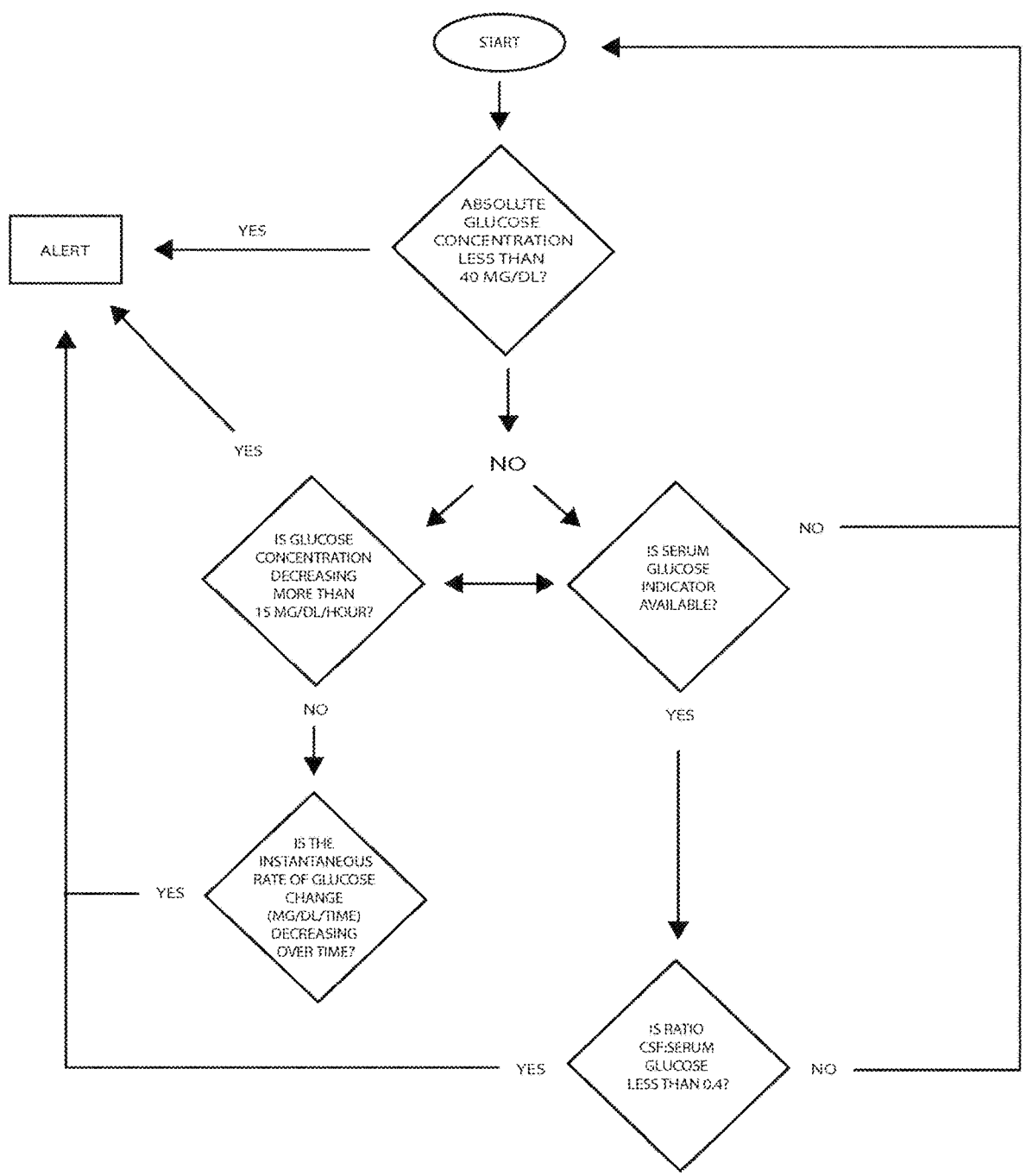

FIG. 10 shows one embodiment of an algorithm that is programmed into the control circuitry of the computational device when the catheter is coupled to a cerebrospinal glucose or lactate sensor. This allows for monitoring and reporting of changes in cerebrospinal fluid glucose or lactate concentration, which can predict infections in the cerebrospinal fluid. The algorithm allows the computational device to notify the patient or medical personnel of an impending infection.

Figure 11:
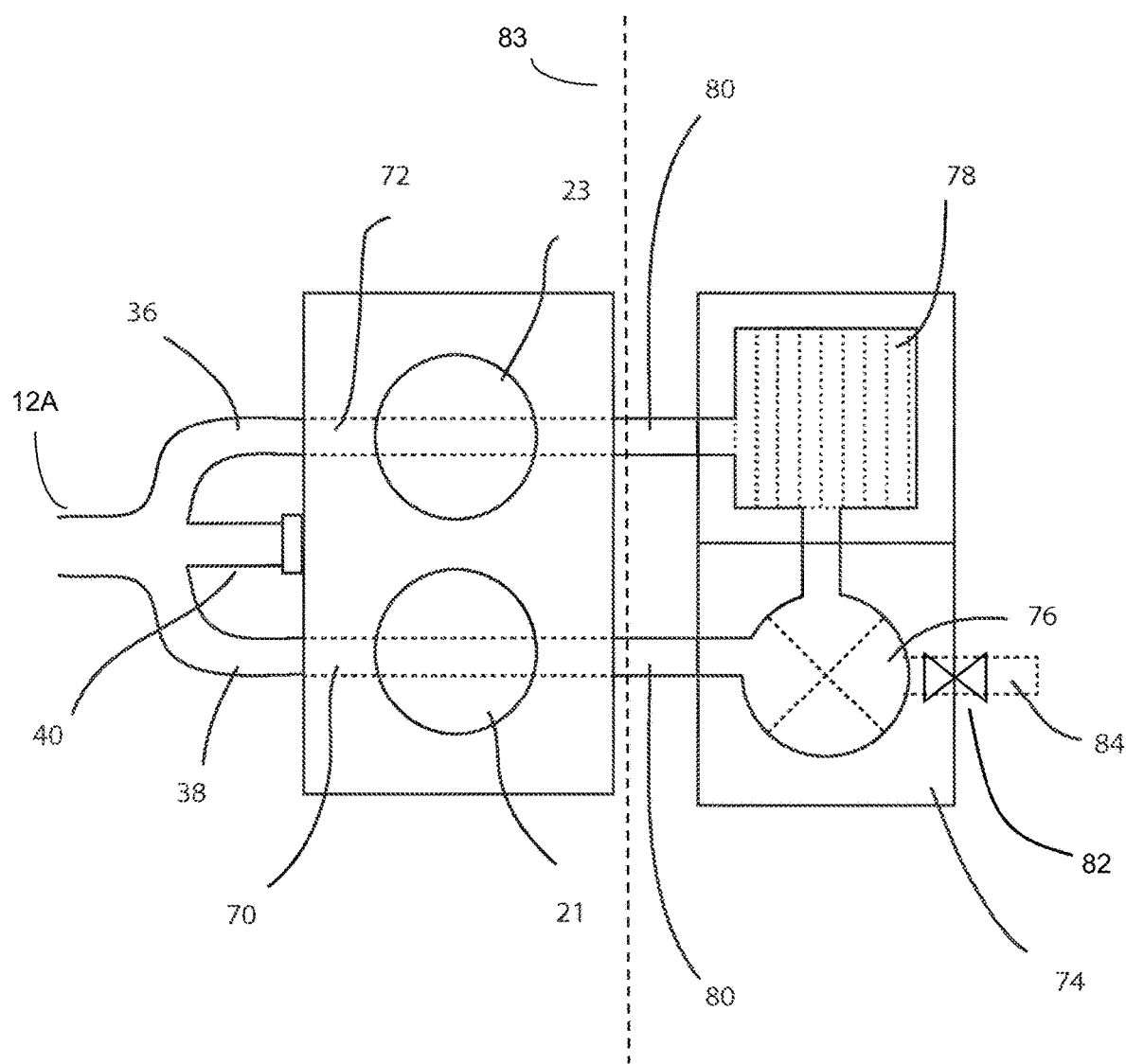

FIG. 11 shows one embodiment of the lumbar catheter and subcutaneous dual reservoir/pump coupled to another medical device, which in this instance may be a cerebrospinal fluid pump and dialyzer, optionally connected to a distal shunt catheter.

DETAILED DESCRIPTION OF THE INVENTION

The following list of elements is consistently used throughout the drawings.

LIST OF ELEMENTS

10 Wireless data transmitter
11 Subcutaneous dual reservoir/pump, here fastened to the posterior ilium
12 Lumbar intrathecal catheter coupled with medical probe
12A Catheter, with or without a medical probe, with one or more lumens, and at least one distal fluid opening and proximal fluid opening, configured for access to patient cerebrospinal fluid in arbitrary locations.
13 L4/L5 interspace
14 Wireless data
16 Wireless data receiver
17 Wireless data transmitter (controller) with one or more control buttons (17A)
18 Wireless data display
19 Computational device algorithmic detection of falling glucose concentration over time
20 Subcutaneous dual reservoir/pump and computational device assembly
21 Fluid inflow reservoir, which may be a pumpable dome
22 Fastener to anatomic surface
23 Fluid outflow reservoir, which may be a pumpable dome
24 Catheter wire port connecting to embedded computational device surrounded by needle impervious material
26 Needle impervious material
27 Reinforced needle impervious base
28 Fluid inflow to a catheter connector
29 Fluid outflow to a catheter connector 30 Medical probe (sensor) and wire along the axis of a catheter
32 Fluid outflow section
34 Fluid inflow section
36 Fluid outflow to reservoir connector
38 Fluid inflow to reservoir connector
40 Medical probe wire connector
42 Medical instrument (sensor)
44 Fluid circuit
46 Energy waves
48 Diseased or injured tissue
50 Surgical tool
52 Computational device circuitry (e.g. a computer processor, configured with appropriate software)
54 Input/Output circuitry
56 Control circuitry (e.g. a computer processor configured with appropriate software)
58 Communications circuitry
60 Memory
62 Storage
70 Inline inflow conduit
72 Inline outflow conduit coupled with check valve, flow meter, and integrator
74 Pump and dialyzer assembly
76 Pump
78 Optional dialyzer
80 Check valve/flow meter
82 Valve which shunts fluid to an optional conduit 84 when the fluid volume and/or fluid pressure is high
83 Dashed line showing an optional location of the patient's skin. In some embodiments, devices to the left are implanted, and devices to the right are external to the patient's body. In other embodiments, everything may be implanted, and thus dashed line (83) is not present.
84 Optional conduit to a traditional distal shunt catheter toward a drainage bag, peritoneum, pleura or atria
100 'Work' section at the tip of a catheter
102 Cap-height
104 Cap-radius
106 Reservoir-perimeter
108, 110 catheter connecting fluid passageway
200 'Bulk fluid exchange' middle section of a catheter
300 'Connector' rear section of the catheter
END OF LIST In the discussion below, it will be useful to refer to FIGS. 5A, 5B, and 5C, as well as FIG. 6.

In the most general form, the present invention may be viewed as being a patient implantable device (20), system, or method for chronic access to a human patient's cerebrospinal fluid. For example, the present invention may be a device comprising at least one (e.g. one or more) fluid conducting catheters (12A, 28, 29), configured to do any of administering a drug or sampling cerebrospinal fluid.

Here, each of these one or more catheters will comprise at least one catheter proximal end (36, 38) in fluid communication with any of a fluid reservoir, fluid pump, or a combination reservoir/pump (21, 23). Each catheter (12A) will also comprise a catheter distal end, with at least one opening (32, 34), configured for placement along a cerebrospinal pathway of the patient.

The device will further comprise at least one fluid reservoir (21, 23). Typically, this at least one reservoir will comprise a hollow dome (21, 23) configured to store fluid. This hollow dome will typically comprise a substantially spheroidal cap with a cap-height (102) and a substantially flat cap base with a cap base radius (104). This cap base radius defines a reservoir perimeter (106) that is substantially perpendicular to the cap-height (102). Each of these one or more reservoirs (21, 23) is mounted on a rigid support (26—sometimes called the needle impervious material). This rigid support is also substantially (e.g. within about +/−15 degrees) parallel to the various reservoir perimeters (106).

Each reservoir further comprises at least one catheter connecting fluid passageway (108, 110), substantially parallel to the rigid support (26), that connects to a catheter proximal end (e.g. 36, 38) of a catheter (12A). This device is configured to perform at least one of the following:

1) Administer drug from at least one reservoir thorough a distal end of a catheter to the patient's cerebrospinal fluid. Note that for simplicity, the one or more fluid ports (FIG. 6, 200) located near (e.. near the last 10-20% of the catheter's length), such as FIG. 6 (32, 34) are also referred to as the "distal end". Thus fluid administration through the "distal end" does not have to be exactly at the extreme distal end of the catheter, but rather can be though one or more fluid ports that are located on the distal side of the catheter.

2) Alternatively, or additionally, sample the patient's cerebrospinal fluid through the distal end of a catheter, and store this sampled cerebrospinal fluid in at least one reservoir.

The invention thus provides a device, system, and method for treating neurological disease or other diseases with an indwelling lumbar intrathecal catheter, optionally coupled to a medical probe, that is tunneled to a subcutaneous reservoir/pump that in an exemplary embodiment would be fastened to the posterior ilium.

In some embodiments, the invention allows for simultaneous inflow and outflow of cerebrospinal fluid, which would allow for the treatment and exchange of cerebrospinal fluid. The system and method may be used in isolation or in line with other specialized devices such as internal subcutaneous valves, anti-syphon technology, pumps, drug delivery systems, filters, and dialyzers. Alternatively, the subcutaneous reservoir/pump can be accessed by an operator externally with needles and external pumping, drug delivery, filtering and/or dialyzing of the cerebrospinal fluid may take place. Alternatively, in some embodiments, artificial cerebrospinal may be injected for treatment of medical conditions such as cerebrospinal hypotension. In such situations, the dialysis device may not be necessary.

In some embodiments, the one or more reservoirs (21, 23) can comprise a resealable material or port configured to admit an injection needle. This injection needle is typically configured to either introduce fluid (drugs, artificial cerebrospinal fuid) or remove fluid from this at least one reservoir, and to reseal after this injection needle is removed, thus preventing leakage of fluid from the at least one reservoir after the injection needle has been removed.

In some embodiments, the subcutaneous reservoir/pump can be configured to allow for simultaneous, bidirectional cerebrospinal fluid access and flow and therefore cerebrospinal fluid exchange. In some embodiments, the invention also allows for analysis of physiological data with an onboard computational device (e.g. processor), appropriate probes/sensors, and allow for wireless, sonic, or infrared transmission of physiological data and warning signals.

The system and method can also be configured to allow for the wireless transmission of physiological data. The system and method can also be configured to accept commands from an external controller (see FIG. 2B, 17)

Approximately 5-10% of all cancer patients will develop epidural metastases at some point during their disease course, and this is associated with debilitating pain. In adults, the most frequent cancers associated are breast, lung or prostate cancer. Metastatic pain from epidural metastases can be treated with local injections, which reduces the systemic complications associated with intravenous routes. See for example, Gupta M. *Role of Early Caudal Epidural in Epidural Metastasis Mediated Neuropathic Cancer Pain. Delineating the Safety and Efficacy Measures. Indian J Palliat Care.* 2015; 21(3):359-360. doi: 10.4103/0973-1075.164899. Although patient controlled analgesia from an external pain pump via an intravenous route is previously known in the art, such prior art approaches require a patient to be attached to an external pain control unit.

By contrast, according to the present invention, indwelling (implanted) units, such as those taught by the present invention, equipped to receive commands from an external wireless controller (FIG. 2B, 17) configured for either patient and/or medical provider use, would improve medical options in pain and palliative care, and allow for increased patient autonomy.

Figure 1:
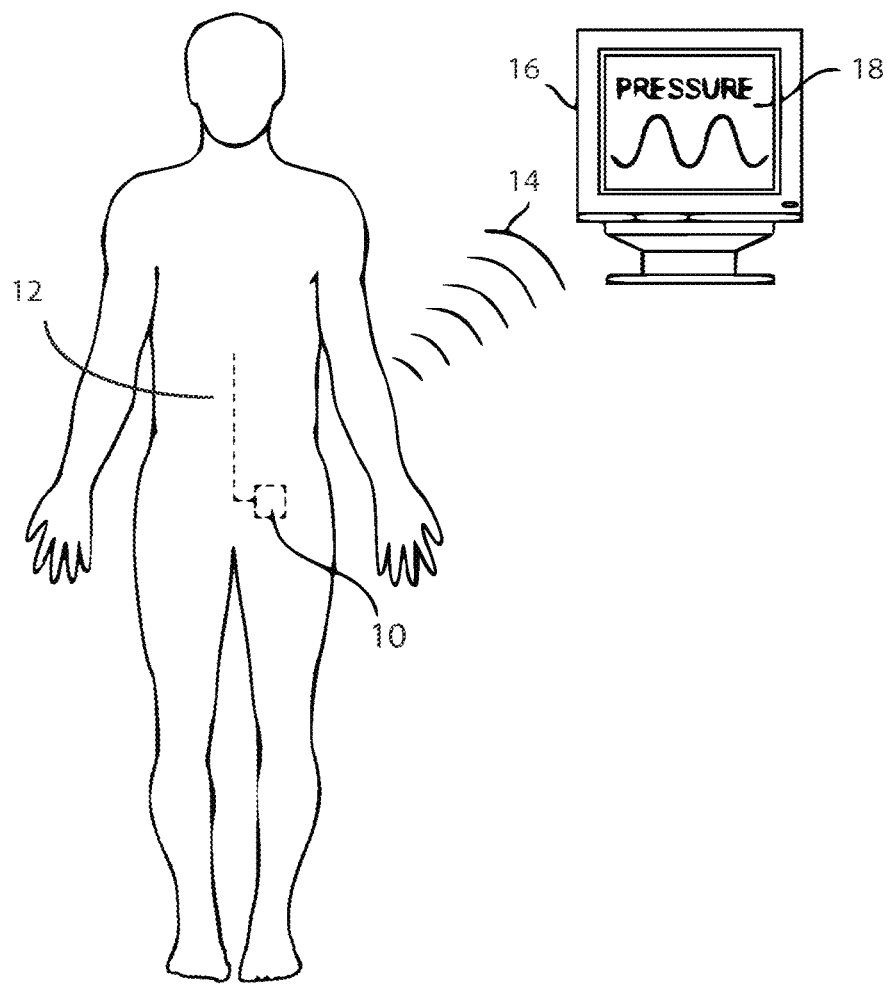
FIG. 1 is a diagram of a patient with implanted lumbar catheter coupled to a medical probe type sensor configured for sensing intrathecal pressure, the probe of which sends data by wire to a subcutaneous dual reservoir/pump device. In this example, a wireless transmitter on the assembly (device) sends information on cyclical changes in the intrathecal pressure to an external display.

FIG. 1 demonstrates a patient with an indwelling lumbar catheter with a medical probe (sensor) tunneled to a subcutaneous dual reservoir/pump. In this non-limiting example, the lumbar catheter is coupled to a pressure transducer at the tip of the catheter, which is connected by a data transmission wire running along the catheter to the invention's pump device. In this embodiment, the pump device also houses a computational device (e.g. processor) and circuitry configured to transmit data wirelessly. This control circuitry allows the analysis of the data, and the generation of warning signals in event the physiological data falls outside of expected norms. In this example, the wireless data (14) is sent to a receiver (16), and then to a display (18). Changes in pressure and compliance can be monitored with suitable sensors and can be compared to norms stored in computer memory, as well as computer modeled expected values. If the actual data falls outside the expected norm, the system can be configured to automatically generate a warning signal and transmit this wirelessly to the patient or medical personnel. Alternatively, an audible or tactile signal could be generated.

In an exemplary embodiment, would a pressure meter (sensor or probe) may be housed at the catheter tip. This pressure probe or sensor would move with the patient, and not be subject to the positional reference changes that can affect external pressure transducers (sensors). The pressure meter could be a transducer, sensor and/or other microelectromechanical systems device.

Other medical probes (sensor) embodiments and combinations are possible. Alternative types of medical probes/sensors can be used that are configured to measure pH, temperature, CSF gas values, oxygen, $CO_2$, pressure, flow, volume infused and/or withdrawn, cerebrospinal fluid volume or impedance sensor, cardiac cycle, respiratory cycle, circadian rhythm, concentration of fluid, tonicity, osmolality, osmolarity, craniospinal compliance, cranial compliance, spinal compliance and the like. Other probes or sensors may comprise a MEMS device where the lumbar catheter meets the dura monitoring dural pulsations and dural compliance; or a conductivity sensor where the lumbar catheter meets the dura monitoring changes in dural conductivity with pulsations in the CSF and thus dural compliance. Still other types of probes/sensors may monitor protein concentrations, glucose, lactate, bicarbonate, gyro-position sensor or gyroscopic sensors, amino acids, alphaketoglutaric acid, magnesium ions, calcium ions, sodium ions, potassium ions, chloride ions, gamma aminobutyric acid, and other amino acid concentrations. In some embodiments, multiple probes/sensors, configured to monitor electrical admittance/impedance between probes to gauge contact with tissue or catheter migration, may be used. Other types of medical probes could also record the incoming ICP wave, and the like, via using coupled medical instrument feedback so as to produce standing waves type waveforms.

Some medical probes can also be visual guides or imaging devices. These can include ultrasound transducers, cameras, infrared sensors, photoacoustic imagers, imagers with a plurality of light fibers surrounding the catheter, and acoustic transducers. In some or all of these cases, data from these medical probes could be processed by the computational circuitry, and used to alert the patient or medical personnel, and/or be used to control fluid control actuators (e.g. pumps, valves under computer processor control) to enact changes to bring the patient's physiological state back to equilibrium.

Combinations of medical probes are possible, and combinations of the same type of probes may be used as well. For example, the same probe may be used at both the tip (distal side) and base (proximal side) of the catheter. With the latter, the signals from the respective probes could be compared to each other to cancel out noise, as well as be compared to an external signal.

Here, for example, pressure transducers in the intrathecal space can be used to register a pressure waveform that results from the patient's cardiac pulsations. An external cardiac monitor, such as an oximeter or other-type cardiac waveform analyzer, such as an EKG or echocardiogram, could also be co-analyzed with the intrathecal pressure measurements to cancel out noise. Moreover, various types of mathematical transfer functions can be programmed into the embedded computational circuitry (processor). These can be used to compute an expected intrathecal pressure waveform based on the expected cardiac output. The processor can then compare this computationally to the actual waveform as observed by various sensors. The processor can be further configured so that deviations from the expected results can be used to alert the patient or medical personnel of the change. This data could also be used to signal embedded actuators, such as processor-controlled or pumps in the device, to take a course of action to remedy the situation.

In the non-limiting example of a fluid or drug pump in the intrathecal space, the intrathecal pressure follows a trajectory known as the compliance curve, which represents the change in pressure which results from a change in volume of the system. Initially, small volume increases produce small pressure increases, but beyond a critical value, even small changes can produce dramatic increases in intrathecal pressure. Therefore, with suitable sensors and computational algorithms, the invention may be used to monitor the average intrathecal pressure vs. the pulse intrathecal pressure, which tends to increase as the brain and spinal cord become less compliant. Here, the system's computational circuitry could be further configured to reduce the flow of fluid in the system as the compliance decreases.

Alternatively, in cases where the medical probe(s) further includes a volume sensor type probe, the system can be configured to alert for additional fluid pumping or needle injection, or alternatively can be configured to shut an outflow valve temporarily, such as until the volume is increased endogenously through the natural cerebrospinal fluid production mechanisms.

Additionally, it is known that various intracranial/intrathecal spinal parameters vary with physiological cycles and patient position. Thus, alternative embodiments of the system may include computational circuitry that identifies the components of the pulsatile intraspinal or intracranial pressure, and then gates the opening of a cerebrospinal fluid valve according to the patient's cardiac and/or respiratory cycle.

Here, for example, the confluence of the patient's cardiac and respiratory cycle peaks are thought to result in Lundberg C waves, which are transient spikes in intracranial and/or intrathecal pressure. Thus, if the volume of CSF is determined to be normal, the computational circuitry can be configured to temporarily shut a cerebrospinal fluid valve during the peak cardiac and respiratory activity, thus preventing overdrainage of the cerebrospinal fluid. This overdrainage is a known morbidity (problem) of present medical art.

Moreover, the computational device can be further configured to compute the average intracranial or intraspinal pressure over time, and adjust the valve automatically with actuators on the device (e.g. a using processor-controlled valve) and open the valve intermittently between episodes of the pulse ICP to prevent overdrainage.

Position (e.g. position with respect to gravity) sensors (e.g. gyroscopic sensors, accelerometers) could also be used as sensors, and the device processor configured to prevent overdrainage while the patient is recumbent, by altering the valve opening pressure based on a patient's position. The device computational circuitry can also be configured to evaluate the components of ICP waveform to identify the position of the system along the compliance curve.

Those skilled in the art know that three components of the waveform P1, P2 and P3 are recognized, with the first being the percussive, the second being the tidal, and third representing the dicrotic notch. Increases in the P2/P1 ratio, as identified by the various medical probe (sensors) and the device's computational circuitry, would indicate lower compliance and would allow suitable actuators (such as processor-controlled valves) to return the system to equilibrium. For example, the processor may command a computer-controlled pump or valve to reduce the pump rate, or increase fluid egress, or alternatively notify a patient or medical personnel of the problem.

Computational circuitry, such as a computer processor configured with appropriate software, could monitor the patient's heartbeat beat-to-beat variation of the intracranial or intraspinal waveform and perform a Fourier transform, which would identify the power in the respective harmonics. Increases in the power of the first harmonic of intracranial or intraspinal waveform would indicate lower compliance and could alert the patient or medical personnel or autonomously effect actuators to return the patient's system to equilibrium. This can be done by reducing the inflow of fluid into the craniospinal system or increasing the outflow of the fluid from the craniospinal system, or by triggering a recalibration step of the equipment.

Finally, although many features or descriptions described above can be in the context of a lumbar approach to the cerebrospinal fluid, it will be understood that features or descriptions can be applied to a variety of settings, including the cranioventricular, cisternal or venous sinus approaches. Thus monitoring the heartbeat beat-to-beat variation of the intrathecal pressure could be used as a means of gauging the stability of the system and could guide therapeutic endeavors.

input/output circuitry 54), and to use this sensor information to perform various functions, such as:

1) Transmit (FIG. 9-58, FIG. 1-14, FIG. 2A-14) at least some of this information outside the patient's body by any of a wireless, light, sonic, ultrasonic, or infrared signal.

2) Alternatively, or additionally, regulate a flow of fluid, typically by using a processor-controlled actuator such as a processor-controlled valve or pump (e.g. 72), between the at least one catheter and the at least one reservoir.

The dome design can be configured to allow for access with a Huber-type needle as well as priming with finger ballotment. Here, an additional improvement over prior art is that bidirectional fluid inflow and outflow are now possible, thereby allowing cerebrospinal fluid exchange.

Note that in some embodiments, as previously discussed, to support the communication functionality previously disclosed, the device may comprise at least one computational device processor, and this at least one processor may be further configured with communications circuitry (58) that includes a wireless or infrared receiver/transceiver configured to receive device control information from outside the patient's body. Here the at least one device processor can be configured to use this control information to regulate (often by using a processor-controlled actuator such as a valve or pump) the flow of fluid between the at least one catheter (e.g. 12A) and the at least one reservoir (21 or 23).

Figure 2A:
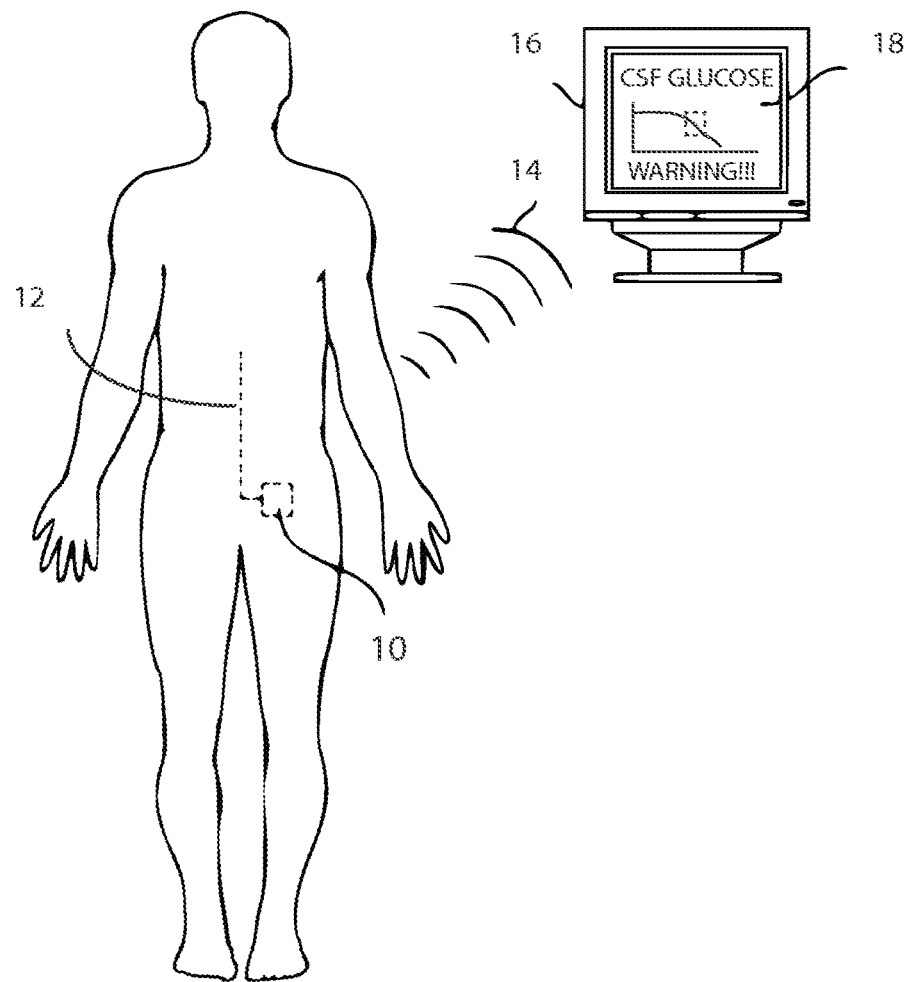
FIG. 2A is a diagram of a patient with an implanted lumbar catheter coupled to a medical probe configured to sense cerebrospinal glucose. This probe sends glucose data over a wire to a subcutaneous dual reservoir/pump device. The device's wireless transmitter sends information on glucose concentration to a display. The control circuitry on the assembly sends a warning signal to a patient and/or to medical personnel that an infection is imminent.

FIG. 2A demonstrates an alternative embodiment where the lumbar catheter is coupled to an intrathecal glucose sensor. Changes in cerebrospinal fluid glucose concentrations are diagnostic of infections of central nervous system. Indwelling medical devices of the CNS are prone to infections. Currently, infections are dealt with after they have been initiated. This embodiment would allow the continuous or intermittent monitoring of CSF glucose values via one or more intrathecal glucose sensors. Reusable implantable glucose sensors are known in the art. Such methods glucose-sensing, and other chemical analyte sensing, include enzymatic, ultrasound, conductivity, heat capacity, electrical stimulation, impedance spectroscopy, photoacoustic, spectrophotometry and/or optical.

As previously discussed, the one or more medical probe (sensors) would connect (send data) over a catheter data wire connection to the subcutaneous dual reservoir/pump which houses communication circuitry. The computation device (processor) could analyze the signal algorithmically, such as exemplified but not limited to FIG. 10, which shows one embodiment of such an algorithm. If a warning level is triggered, the patient or medical provider would be alerted with a wireless signal. Alternatively, an auditory or tactile signal can be enacted with built-in sonic or haptic actuators.

Figure 2B:
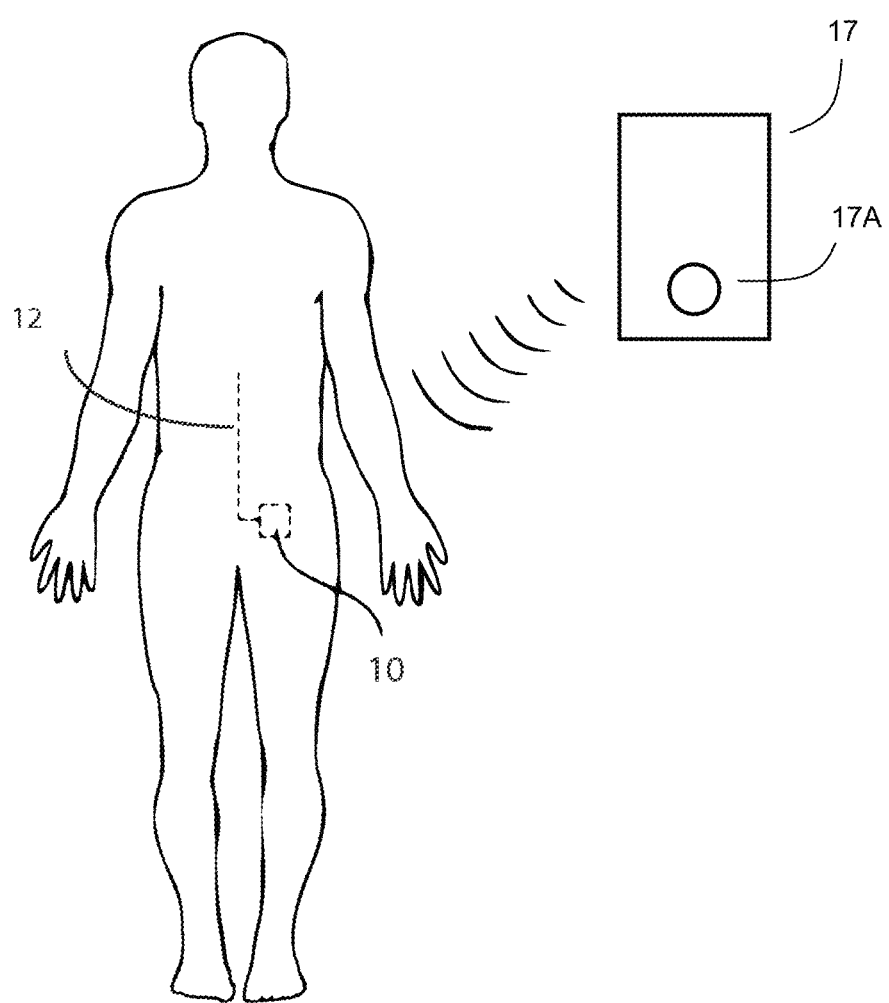
FIG. 2B shows an alternative embodiment, in which the device comprises a wireless receiver configured to receive commands from an outside controller, such as a patient or healthcare provider controlled wireless transmitter, which controls the release of one or more drug stored in one or more of the device's reservoirs.

FIG. 2B shows an alternative embodiment, in which the device comprises a wireless receiver configured to receive commands from an outside controller (17), such as a button activated (17A) patient or healthcare controller, which controls release of drug that has stored in one or more of the device's reservoirs.

Figure 3:
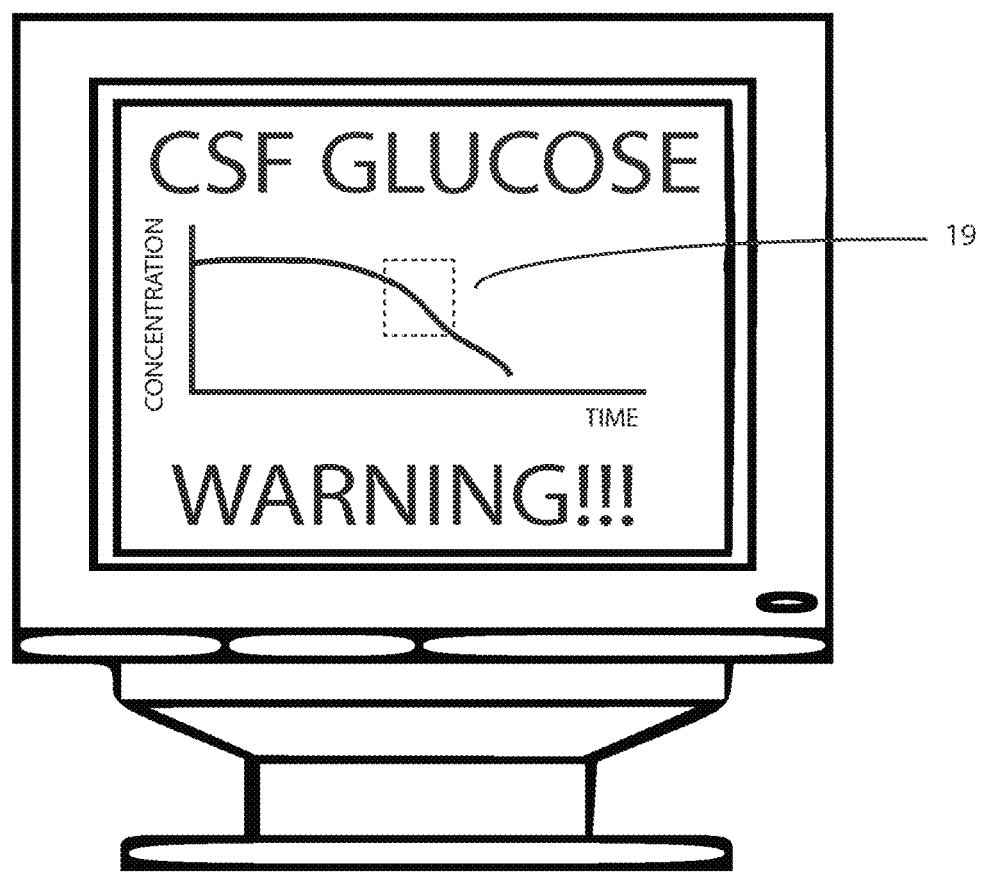
FIG. 3 is a magnification of the display in FIG. 2A (16). The display shows the concentration of glucose over time.

FIG. 3 demonstrates a higher magnification of the display previously shown in FIG. 2A. This display allows a patient or medical provider to receive alarms and date fom the system's computational device, such as when the device is alerted (from catheter sensor readings) of a critical change in the patent's cerebrospinal glucose concentration.

FIG. 4 demonstrates an exemplary embodiment of the anatomic placement and configuration of the invention's system and method. The distal end of a lumbar catheter, coupled to a medical probe is placed in the patient's lumbar interspace, preferentially the L4/L5 interspace. The proximal end of the catheter is tunneled to another location, an exemplary embodiment would be the posterior ilium. The ilium provides a convenient chronic access point along with a well-known anatomic landmark. The tunneling reduces infection and minimizes destruction of tissue.

When compared to the prior art Ommaya cranioventricular catheter and device, the invention has many advantages. The implantation operation or procedure needed to implant the present invention's device is much easier on the patient. For example, only local anesthesia would be necessary, along with less OR and recovery time. No cranial access is required, so there is less risk of catheter migration into the brain. Furthermore, the configuration is hid by the patient's clothes, unlike the head located and cosmetically distressing Ommaya device, thus improving cosmesis.

Another advantage of the present invention is that it enables use of a lumbar location, which is also less prone to overdrainage of cerebrospinal fluid and is a natural reservoir for CSF.

Indeed the lumbar location is typically more compliant to fluid infusion than patient's brain and brain ventricles which are housed in the patient's fixed skull.

Finally, if a multiple (e.g. dual) dome configuration is used, the dual dome configuration enables a subcutaneous reservoir/pump which allows for chronic access and simultaneous fluid inflow and outflow. The invention's device can also be hooked up (using a dual needle arrangement) to an external pump, or dialyzer, or filter for CSF exchange, as well as for continuous drug delivery.

The multiple (dual) dome configuration also provides a means to assess patency of the catheter tubing. Further, the multiple (dual) dome configuration also enables reversal of the pumping cycle, which is helpful to clear any obstructions in the catheter or other tubing, which is a fairly common occurrence.

Other alternative embodiments could include use of an internal or external impeller to break up any clots or other obstructions. Ideally, this clot-busting technology should be configured to break up debris to dimensions of about 10 microns or less, in order to allow for easy aspiration and minimize trauma to local structures.

The invention's dome device may be implanted in other patient body areas as well. Other embodiments of anatomic placement include the patient's subcutaneous lower abdomen, along the vertebral column, surgically fixed to a lamina or pedicle, or other structural-element of the vertebral column. The device may be fastened to an anatomic structure by any art-recognized means, including screws, sutures, adhesives, etc.

In some embodiments, radiopaque elements can be placed along any of the components to guide its evaluation with plain X-ray imaging. Another advantage of this invention's system and method is that, relative to the prior art, it needs fewer repeat imaging examinations, such as MRI and/or CT, which are costly, and in the case of CT also expose the patient to undesired radiation.

FIG. 5A demonstrates the subcutaneous reservoir/pump in a multiple dome (such as a dual dome) configuration. The dome shape is exemplary but can be substituted in other embodiments by any suitable geometry. In some embodiments, the dome shape will be that of a spheroidal cap (e.g. a planar cross-section of a hollow spheriod, where the spheriod is defined as a solid generated by a half-revolution of an ellipse about its major or minor axis).

One or more of the domes can be made of a self-sealable material such as silicone. If a pumpable dome is desired, the material should also be elastic so as to be able to deform upon the application of appropriate finger pressure. This enables the previously discussed finger ballotment methods.

More specifically, in some embodiments, the at least one reservoir thus comprises at least one pumpable reservoir configured with a dome comprising an elastic material that is configured to deform to a smaller deformed cap-height in response to external pressure (e.g. finger ballotment) applied to the reservoir (see FIG. 5C). This dome then elastically rebounds to a higher cap-height when the external pressure (e.g. finger ballotment) is removed.

The device can also further comprise a storage reservoir, which may or may not be pumpable, configured with a resealable material or port configured to admit one or more injection needles. This injection needle(s) can be configured to either introduce fluid or remove fluid from the one or more reservoirs, and to reseal after the injection needle is removed, thus preventing leakage of fluid from the reservoir(s) after this injection needle has been removed. In some embodiments, the pumpable reservoir and storage reservoir can also be further configured with at least one reservoir connecting fluid passageway connecting the pumpable reservoir and the storage reservoir.

The two-dome device (FIG. 5A) is thus an embodiment where the device comprises at least one fluid conducting catheter. As before, each catheter will further comprise a catheter proximal end and a catheter distal end with at least one opening at or near the distal end. This catheter distal end is configured for placement along a cerebrospinal pathway of a human patient. This multiple dome configuration will thus comprise a least a first reservoir comprising a hollow dome configured to store fluid. This hollow dome will typically comprise a substantially spheroidal cap with a first cap-height, and a substantially flat cap-base with a first cap-base radius. This first cap-base radius defines a first reservoir perimeter that is substantially perpendicular to the cap-height.

In a preferred embodiment, the second (and any other) reservoirs are mounted on the same rigid support as the first reservoir/dome, and this rigid support mounted in a way that is substantially parallel to the at least first and at least second reservoir perimeters. Typically, each of the reservoirs will further comprise at least one catheter connecting fluid passageway that is both substantially parallel to the rigid support, and that also connects to a catheter proximal end of a catheter. This multiple dome device can be configured to perform any of administering drug from at least one of the first or second reservoirs, through a distal end (e.g. through one or more ports at or near the distal end) of a catheter, to the patient's cerebrospinal fluid. Alternatively or additionally, this multiple dome device can also be configured to sample the patient's cerebrospinal fluid through the distal end of a catheter (e.g. through ports at or near the distal end of a catheter) and store this sampled cerebrospinal fluid in at least one of the first or second reservoirs.

Regarding the rigid support or "body": The body should ideally be constructed to be needle impervious, because it will often encounter wrongly targeted injection needles, and because it often houses sensitive electronics and computational circuitry. These electronics can include a computer processor, which can be hardware or software configured to perform the various operations described in this disclosure. For adequate strength, the housing or body or support (27) can be reinforced a casing of a suitable rigid biocompatible material such as polyethersulfone or other type material. Nitinol or other biocompatible metals can be incorporated into any aspect of the assembly, and nitinol is particularly useful to prevent accidental catheter kinking.

The catheter may also be segmented to prevent kinking or recoil, and some embodiments of the invention may also comprise a catheter that is steerable and lockable.

Additional embodiments of the device may be fitted an antibacterial filter, and/or the component walls may be impregnated with an antibacterial coating. Additionally, the component walls, including catheter fluid apertures and fluid exchange sections, may be treated and impregnated with antiproliferative medications, including immunosupressants such as cyclosporine or rapamycin, or other agents to reduce tissue ingrowth into the device.

In some embodiments, when two or more domes are used, the dual dome configuration can be configured to allow reversal of the pumping cycle to clear obstructions. An alternative embodiment could include an internal or external impeller to break up clots. This clot-busting technology should ideally break up clots or other debris to approximately 10 microns or less to allow aspiration and at the same time minimize trauma to local structures.

The device can also comprise suitable tissue fasteners (22), which can be configured to allow the device to be permanently fastened to an anatomic site.

An alternative, but less functional embodiment would only have a single dome reservoir/pump.

FIG. 5B shows the alternative, but less functional embodiment that only has a single dome reservoir/pump, previously discussed in FIG. 5A.

As previously discussed in FIG. 5A, suitable tissue fasteners (22) allow the device to be permanently fastened to an anatomic site. Put alternatively in some embodiments, the device (20) may further comprise rigid support (26), configured with at least one tissue fastener loop or opening (22). At least some of these loops or openings (22) may be configured to help fasten device (20), by any of screws, sutures, or adhesives, to an anatomic site comprising any of a patient's lumbar vertebrae, posterior ilium, lamina, or pelvis (see FIG. 4, 11).

The dome shape is exemplary but can be substituted in other embodiments by any suitable geometry. The domes should be made of a self-sealable material such as silicone. When implanted under the skin, the device will frequently be exposed to injection needles, which may not always be aimed properly. Thus, as previously discussed, the housing, body or support (27) should preferably be needle impervious, because it houses sensitive electronics and computational circuitry.

In the single dome configuration shown in FIG. 5B, the device comprises at least one fluid conducting catheter (and indeed will often be just one catheter). This catheter comprises a catheter proximal end and a catheter distal end, with at least one port opening at or near the distal end. As previously discussed, this catheter distal end is configured for placement along a cerebrospinal pathway of a patient. This as per the multiple dome device, the single dome device also comprises a reservoir comprising a hollow dome configured to store fluid. This hollow dome also comprises a substantially spheroidal cap with a cap-height, and a substantially flat cap-base with a cap base radius. This cap-base radius defines a reservoir perimeter configured to be substantially perpendicular to the cap height. This reservoir is preferably mounted on a rigid support configured to be substantially parallel to the reservoir perimeter. This reservoir will further comprise at least one catheter connecting fluid passageway that is substantially parallel to the rigid support, and this passageway connects to a catheter proximal end of the catheter. This device can be configured to administer drug from the reservoir, through ports at or near the distal end of the catheter, to the patient's cerebrospinal fluid. Alternatively or additionally, the device can also be configured to sample the patient's cerebrospinal fluid (through ports at or near the distal end of this at least one catheter) and storing this sampled cerebrospinal fluid in the reservoir.

FIG. 5C shows how, in some embodiments, at least one reservoir dome can comprise an elastic material configured to deform to a smaller deformed cap-height (102S) in response to external pressure (such as finger pressure) applied to the reservoir, and then to elastically rebound to a higher cap-height (102) when the external pressure is removed, thus creating a pumpable reservoir. In FIG. 5C, the dome is shown deformed under finger pressure, which has caused the cap height (see FIG. 5B, 102) to deform to a smaller deformed cap height (102S).

Although in some embodiments, the catheter (12A) may be a simple, single lumen catheter with as little as one distal opening, one proximal opening, and no additional sensors, in other embodiments, the catheter may be more complex, as shown in FIG. 6, FIG. 7, and FIG. 8.

FIG. 6 shows an exemplary embodiment of a more complex sensor-equipped multilumen catheter. In this embodiment, one or more medical probes are coupled to the catheter, preferentially at the tip (30). Alternative embodiments may duplicate the same probe at another location on the catheter, such as at or near the catheter proximal end (the base). The signals from the probes can be compared, as desired, to cancel noise and assess position of the catheter.

Computational circuitry can be used to affect actuators (system valves, pumps, alarms, and the like) to bring the patient's physiological parameters back to equilibrium.

In some embodiments, the catheter may be divided into a 'work' section (100), a 'bulk fluid flow/exchange' section (200) and a rear 'connector' section (300). The 'work' section in this exemplary embodiment consists of a medical probe at the tip. Alternative embodiments would allow additional intervention, including end-fire fluid ports capable of pulsatile or oscillatory flow, along with surgical tool ports. The 'bulk fluid flow/exchange' section can comprise a plurality of ports or apertures and can be configured to allow for more than one fluid exchange section which can be separated by a distance to prevent remixing of the clean or desired fluid, or inflowing drug with outflowing cerebrospinal fluid, after treatment.

As previously discussed, in some embodiments the catheter is segmented or can contain motile elements for steering, maneuvering and locking without recoil. Aspects of the catheter can be reinforced with nitinol to prevent kinking. Additional tool ports and/or medical instruments can be placed along the 'bulk fluid flow/exchange' section. The rear section in this exemplary embodiment includes inflow (38) and outflow (36) and an electrical connector (40) which connects the wire from the medical probe to the embedded computational circuitry of the subcutaneous dual reservoir/pump.

FIG. 7 demonstrates an alternative embodiment of the 'bulk fluid flow/exchange' section where a medical instrument has been incorporated between two fluid exchange sections. This configuration can include but is not limited to, systems for photoactivation of medications, cooling of tissue that may be heated by the medical instrument or fluidic pulses to counteract negative pressure and microbubble formation by the medical instrument. The medical instrument can be placed anywhere along the catheter and can be configured to send and receive energy in any art-recognized form. This includes, but is not limited to, acoustic, radiofrequency, ultrasonic, high-frequency ultrasound, photoacoustic, infrared, infrared differential interference contrast, visible light, laser, Raman spectroscopy, and optical coherence tomography, The invention's fluid circuit can be configured to vary the volume infused over time, as well as the temperature and concentration of fluids which can be timed and coupled to energy pulses, thereby allowing novel combination therapies. Energy can be delivered at a resonant frequency of a target at desired power and duration, including sweeping above and below that frequency, until the desired effect is achieved, such as eradication of an infection or tissue growth.

Another embodiment of this system would comprise a steerable catheter that further includes fiducial adhesives that are placed on a patient along key anatomic landmarks of the head, neck, shoulders, and pelvis. After imaging with the fiducials, the data is fed into a computer with imaging data along with surface fiducial landmarks. Thereafter, fiducials emitting energy toward the spinal or cranial pathway can be placed on the initial adhesive (e.g., when MRI makes any metal-containing fiducials incompatible). These sonic fiducials can transmit energy that can be picked up by one of the medical probes on the catheter, which then will be fed to the computational device and computer, along with original imaging, to get a sense of the position of the catheter. This can reduce the amount of radiation a patient experiences due to repeat fluoroscopy.

FIG. 8 demonstrates another embodiment of the catheter with an end-fire aperture, and lumen configured to acting as a sheath to pass other surgical tools. These surgical tools can be visualized with the catheter's medical probe or sensors, and the surrounding tissue can also be visualized with the catheter probes or sensor to prevent any injury.

If the surgical field is bloody, a plain camera could not visualize very much, and in this case, an imaging modality able to penetrate to some depth in bloody surgical fields, such as ultrasound-based sensors, would be helpful.

The surgical tool passed through the catheter's surgical tool passing sheath include, but are not limited to, microscissors, microscalpels, needles, lasers (optical fibers), electrothermy, radiofrequency ablation, suturing tools, microneedles, X-ray devices, brachytherapy pellets, RF generators, microwave generators, acoustic generators, cryablation-lasers or other type surgical tools.

Although many features or descriptions described above can be in the context of a lumbar approach to the cerebrospinal fluid, it will be understood that features or descriptions can be applied to a variety of lesser invasive surgical approaches, including acute surgeries applied to but not limited to the cranioventricular, cisternal or venous sinus approaches. Moreover, the features or descriptions can be applied to other body vessels, lumens, cavities and tissues for lesser invasive diagnostics and therapeutics.

In some embodiments, the surgical tool and the distal end of the one or more catheters may be configured to guide placement of the catheter (in particular the catheter distal end) to various regions in the patient, such as any of the patient's intrathecal space, the patient's lumbar interspace, and the patient's epidural space between the patient's spinal cord and bones. For example, in some embodiments, the surgical tool may be a guidewire. Here, any of the surgical tool lumen sheath, or the catheter distal end of the one or more catheters, may be further configured to interface with this guidewire. The guidewire, in turn, may be configured for placement in these various regions of the patient, such as any of the patient's intrathecal space, the patient's lumbar interspace, and the patient's epidural space between the patient's spinal cord and bones.

FIG. 9 demonstrates the computation circuitry of the device which incorporates input/output circuitry, control circuitry, communications circuitry, as well as memory and storage. The computational device can be embedded with mathematical models (e.g. algorithms) of the desired system and actual measured parameters can be automatically judged by the device processor against expected values. The system can be configured so that deviations from the norm can be transmitted to outside receivers, and from there to the patient or medical provider. The computation circuitry can thus be configured to send telemetric data to alert a patient or provider of warning signals (often obtained using device sensor data). Moreover, the computational device can receive signals (e.g. commands) from the medical provider in order to change variables and actuator settings. These signals or commands can include commands to open a shunt valve, or can simply comprise commands to query historical data stored in the device memory. For security, in a preferred embodiment, access should be password protected.

Thus in some embodiments, the device can comprise at least one catheter connecting fluid passageway that further comprises a valve. This valve can be configurable for any of: one-way reservoir-to-catheter flow, one-way catheter-to-reservoir flow, or bidirectional fluid flow between the reservoir and the catheter. This valve can be configured (e.g. to open or close, or to implement one-way or bidirectional fluid flow) by various methods, including external pressure, external magnetic force, or (as discussed above) by electronic control by at least one computational device processor or other-type computational circuitry.

FIG. 10 demonstrates an algorithm for the analysis of the patient's cerebrospinal glucose concentration, which is an important variable when assessing for infection. This algorithm can be stored onboard the device's memory, for use by the device's processor.

According to the invention, the invention would allow for the continuous and intermittent measurement of CSF glucose values and the reporting of any critical changes. The system and method would also allow for the comparison of CSF glucose values to an external non-CSF source via telemetric data, allowing the computation of a CSF:serum ratio, whereby a value lower than 0.4 notifies a patient or medical personnel. Tables can be adjusted in the cases of newborns, where a ratio below 0.6 is considered abnormal.

FIG. 11 demonstrates an alternative embodiment of the invention, whereby the device's lumbar catheter, here configured with one or more medical probes, and the invention's subcutaneous dual reservoir/pump assembly, are coupled with another medical device. This "another medical device" can comprise but is not limited to, any of a CSF pump, filter, dialyzer, valve, or drug pump. The "another medical device" can be placed in series or parallel with the invention.

FIG. 11 shows how a CSF pump and optional dialyzer assembly can be added to the invention's subcutaneous dual reservoir/pump system, or even comprise part of the invention itself. Feedback from the invention's medical probe, or received commands, can guide the computational circuitry on when to open up the valves (72) and (80). The valve could check the flow of fluid.

In some embodiments, the CSF pump and dialyzer assembly may external to the patient, and connected to the patient by needles along (80) that are inserted into the device's one or more domes. In other embodiments, a CSF pump and/or dialyzer may be implanted, or indeed by made part of the dome device itself. The dashed line (83) distinguishes between these two possibilities. When the CSF pump and dialyzer are external to the patient, the dashed line (83) indicates the patient's skin, and the devices to the left of the dashed line (83) are subcutaneous devices. When the CSF pump and optional dialyzer are themselves implanted into the patient, then the dashed line (83) indicating the patient's skin is not present, because all devices may be subcutaneous, including the pump and dialyzer, may be implanted.

As is known to those skilled in the art, constant infusion tests have demonstrated that patients tolerate low flows up 0.76 ml/min, so this could be a target for net flow rate. For example, in the case where the invention's medical probe has detected a change in pH or increasing concentration of certain metabolites (e.g., beta amyloid), then the system can be configured so that pump/dialyzer (76) would start working. If an invention's volume sensor/medical probe detects low volume, the pump would stop to prevent overdrainage, and could also alert the patient or medical personnel.

An alternative embodiment would add an additional fluid conduit (84) (similar to 70 and 72) but this time through the pump/dialyzer (76) toward another catheter (e.g. a distal shunt catheter, also labeled 84) which would feed into a drainage bag or simply drain into the peritoneum, the pleura or atrium. This pathway would be actuated by closing valve (82) when the volume sensor indicates increased pressure and volume in the craniospinal compartment.

This invention can thus also comprise a novel and intelligent shunting mechanism. The application of this technology is improved when a medical probe (sensor) is used on the CSF catheter, in conjunction with appropriately configured computational circuitry on the multiple (e.g. dual dome) reservoir/pump. In some embodiments, this device would may otherwise not have no other moving parts add complexity, or to interfere with circuitry.

As previously discussed, in this embodiment as well, the invention's circuitry may also be housed in a needle impervious casing. Additionally, the multiple (e.g. dual) dome system could be utilized to reverse the pumping cycle to remove obstructions of the catheter. Additionally, accessing the system with two needles would allow one to assess the patency of the component catheters by passing a signal through the tubes and assessing the response.

Thus, for example, in some embodiments, the device can further comprise a distal shunt catheter (such as FIG. 11, 84) configured to drain cerebrospinal fluid from any of the various reservoirs (such as FIG. 11, 21) and deposit this cerebrospinal fluid outside of the patient's cerebrospinal regions (e.g. elsewhere in the patient, or even outside of the patient).

Further, in those embodiments where the device comprises at least one controllable distal shunt catheter fluid control valve, the device may be further configured to control this distal shunt catheter fluid control valve (usually by using a computer processor or other computational circuitry) by any of information from at least one sensor or control signals from outside the patient's body.

Although many features or descriptions described above can be in the context of a lumbar approach to the cerebrospinal fluid, it will be understood that features or descriptions can be applied to a variety of lesser invasive surgical approaches, including acute surgeries applied to but not limited to the cranioventricular, cisternal or venous sinus approaches. Moreover, the features or descriptions can be applied to other body vessels, lumens, cavities and tissues for lesser invasive diagnostics and therapeutics.

While the above description contains many specificities, these should not be construed as limitations on the scope of the invention, but as exemplifications of the presently preferred embodiments thereof. Many other ramifications and variations are possible within the teaching of the invention. Additionally, any combination of the above examples may be possible. Thus the scope of the invention should be determined by the appended claims and their legal equivalents, rather than the examples given.

The invention claimed is:

1. A patient implantable device for chronic access to a human patient's cerebrospinal fluid, said device comprising:
   at least one fluid conducting catheter, each said catheter comprising a catheter proximal end and a catheter distal end with at least one opening, said catheter distal end configured for placement along a cerebrospinal pathway of said patient;
   at least one reservoir comprising a hollow dome configured to store fluid, said hollow dome comprising a substantially spheroidal cap with a cap-height, and a substantially flat cap-base with a cap-base radius, said cap-base radius defining a reservoir perimeter substantially perpendicular to said cap-height;
   said at least one reservoir mounted on a rigid support substantially parallel to said reservoir perimeters;
   said at least one reservoir further comprising at least one catheter connecting fluid passageway, substantially parallel to said rigid support, that connects to a catheter proximal end of a catheter;
   said device configured to be completely implanted under said patient's skin;
   said device configured to perform any of administering drug from said at least one reservoir, though a distal end of a catheter, to said patient's cerebrospinal fluid in said patient's cerebrospinal fluid pathway; and/or
   sampling said cerebrospinal fluid through said distal end of a catheter, and storing said sampled cerebrospinal fluid in said at least one reservoir.

2. The device of claim 1, wherein said rigid support is configured with at least one tissue fastener loop or opening, at least one of said at least one tissue fastener loop or opening configured to help fasten said device, by any of screws, sutures, or adhesives, to an anatomic site comprising any of a patient lumbar vertebrae, posterior ilium, lamina, or pelvis.

3. The device of claim 1, wherein said at least one reservoir dome comprises an elastic material configured to deform to a smaller deformed cap-height in response to external pressure applied to said at least one reservoir, and then to elastically rebound to a higher cap-height when said external pressure is removed, thus creating at least one pumpable reservoir.

4. The device of claim 1, wherein said at least one reservoir comprises a resealable material or port configured to admit an injection needle, said injection needle configured to at least remove fluid from said at least one reservoir, and to reseal after said injection needle is removed, thus preventing leakage of fluid from said at least one reservoir after said injection needle has been removed.

5. The device of claim 1 wherein:
   at least one reservoir comprises a pumpable reservoir configured with a dome comprising an elastic material configured to deform to a smaller deformed cap-height in response to external pressure applied to said pumpable reservoir, and then to elastically rebound to a higher cap-height when said external pressure is removed;
   further comprising a storage reservoir configured with a resealable material or port configured to admit an injection needle, said injection needle configured to either introduce fluid or remove fluid from said said storage reservoir, and to reseal after said injection needle is removed, thus preventing leakage of fluid from said said storage reservoir after said injection needle has been removed;

said pumpable reservoir and storage reservoir further configured with at least one reservoir connecting fluid passageway connecting said pumpable reservoir and said storage reservoir.

6. The device of claim 1, wherein said at least one catheter connecting fluid passageway further comprises a valve configurable for any of one-way reservoir-to-catheter flow, one-way catheter-to-reservoir flow, or bidirectional fluid flow between said reservoir and said catheter.

7. The device of claim 6, wherein said valve is configured by any of external magnetic force, or electronic control by at least one computational device processor.

8. The device of claim 1, wherein at least one catheter distal end is configured to guide placement of said catheter distal end to any of said patient's intrathecal space, said patient's lumbar interspace, and said patient's epidural space between said patient's spinal cord and bones.

9. The device of claim 8, wherein said catheter distal end is further configured to interface with a guide-wire, said guide-wire is configured for placement in any of said patient's intrathecal space, said patient's lumbar interspace, and said patient's epidural space between said patient's spinal cord and bones.

10. The device of claim 1, wherein at least one of said at least one catheter is any of a single lumen or multilumen catheter.

11. The device of claim 1, wherein said device further comprises a distal shunt catheter configured to drain cerebrospinal fluid from any of said at least one reservoirs and deposit said cerebrospinal fluid outside of the cerebrospinal regions of said patient.

12. The device of claim 11, wherein said device comprises at least one controllable distal shunt catheter fluid control valve; and said device is further configured to control said distal shunt catheter fluid control valve by information from control signals from outside said patient's body.

13. The device of claim 1, wherein at least one of said at least one catheter, said at least one reservoir, or said rigid support comprises at least one sensor;

said at least one sensor comprising any of a chemical sensor, a reservoir sensor, a rigid support mounted sensor, and a sensor configured to be mounted inside said patient's cerebrospinal fluid pathway;

said device comprises at least one computational device processor, and said at least one processor is configured to receive information from said at least one sensor, and to use said information to perform any of:

a) transmit at least some of said information outside said patient's body by any of a wireless, light, sonic, ultrasonic, or infrared signal;

b) regulate at least one actuator to control a flow of fluid between said at least one catheter and said at least one reservoir.

14. The device of claim 1, wherein said device comprises at least one computational device processor, and said at least one processor is configured with a wireless or infrared receiver configured to receive control information from outside said patient's body;

said at least one processor configured to use said control information to regulate a flow of fluid between said at least one catheter and said at least one reservoir.

15. A patient implantable device for chronic access to a human patient's cerebrospinal fluid, said device comprising:

at least one fluid conducting catheter, each said catheter comprising a catheter proximal end and a catheter distal end with at least one opening, said catheter distal end configured for placement along a cerebrospinal fluid pathway of said patient;

a reservoir comprising a hollow dome configured to store fluid, said hollow dome comprising a substantially spheroidal cap with a cap-height, and a substantially flat cap base with a cap base radius, said cap base radius defining a reservoir perimeter substantially perpendicular to said cap-height;

said reservoir mounted on a rigid support substantially parallel to said reservoir perimeter;

said reservoir further comprising at least one catheter connecting fluid passageway, substantially parallel to said rigid support, that connects to a catheter proximal end of said catheter;

said device configured to be completely implanted under said patient's skin;

said device configured to perform any of administering drug from said reservoir, through a distal end of a catheter, to said patient's cerebrospinal fluid in said patient's cerebrospinal fluid pathway; and/or sampling said cerebrospinal fluid through said distal end of a catheter, and storing said sampled cerebrospinal fluid in said reservoir.

16. The device of claim 15, wherein said at least one catheter is one catheter.

17. The device of claim 15, wherein said rigid support is configured with at least one tissue fastener loop or opening, at least one of said at least one tissue fastener loop or opening configured to help fasten said device, by any of screws, sutures, or adhesives, to an anatomic site comprising any of a patient lumbar vertebrae, posterior ilium, lamina, or pelvis.

18. A patient implantable device for chronic access to a human patient's cerebrospinal fluid, said device comprising:

at least one fluid conducting catheter, each said catheter comprising a catheter proximal end and a catheter distal end with at least one opening, said catheter distal end configured for placement along a cerebrospinal pathway of said patient;

a least a first reservoir comprising a hollow dome configured to store fluid, said hollow dome comprising a substantially spheroidal cap with a first cap-height, and a substantially flat cap base with a first cap base radius, said first cap base radius defining a first reservoir perimeter substantially perpendicular to said cap-height;

at least a second reservoir comprising a hollow dome configured to store fluid, said hollow dome comprising a spheroidal cap with a second cap height, and a substantially flat cap base with a second cap base radius, said second cap base radius defining a second reservoir perimeter substantially perpendicular to said cap-height;

said at least said first and said second reservoirs mounted on a same rigid support substantially parallel to said at least first and at least second reservoir perimeters;

each said reservoir further comprising at least one catheter connecting fluid passageway substantially parallel to said rigid support, that connects to a catheter proximal end of a catheter;

said device configured to perform any of administering drug from at least one of said first or second reservoirs, through a distal end of a catheter, to said patient's cerebrospinal fluid; and/or sampling said cerebrospinal fluid through said distal end of a catheter, and storing said sampled cerebrospinal fluid in said at least one first or second reservoirs.

19. The device of claim 18, wherein said at least one catheter comprises a first and second catheter, said first catheter connecting to a first catheter connecting fluid passageway on said first reservoir, and said second catheter connecting to a second catheter connecting fluid passageway on said second reservoir.

20. The device of claim 19, in which said device is configured for drug flow from said first reservoir to a distal end of said first catheter, and said device is further configured for cerebrospinal flow from said distal end of said second catheter to said second reservoir.

21. The device of claim 18 wherein:

wherein at least said first reservoir comprises a pumpable reservoir configured with a dome comprising an elastic material configured to deform to a smaller deformed cap-height in response to external pressure applied to said pumpable reservoir, and then to elastically rebound a higher cap-height when said external pressure is removed;

wherein said second reservoir further comprises a storage reservoir configured with a resealable material or port configured to admit an injection needle, said injection needle configured to either introduce fluid or remove fluid from said storage reservoir, and to reseal after said injection needle is removed, thus preventing leakage of fluid from said storage reservoir after said injection needle has been removed;

said pumpable reservoir and storage reservoir further configured with at least one reservoir connecting fluid passageway connecting said pumpable reservoir and said storage reservoir.

22. The device of claim 21, wherein said at least one reservoir connecting fluid passageway also comprises a one-way fluid control valve; and/or said at least one reservoir connecting fluid passageway also comprises a fluid control valve or other actuator configured for any of external pressure, external magnetic force, or electronic control by at least one computational device processor.

23. A patient implantable device for chronic access to a human patient's cerebrospinal fluid, said device comprising:

at least one fluid conducting catheter, each said catheter comprising a catheter proximal end and a catheter distal end with at least one opening, said catheter distal end configured for placement along a cerebrospinal fluid pathway of said patient;

at least one reservoir comprising a hollow dome configured to store fluid, said hollow dome comprising a substantially spheroidal cap with a cap-height, and a substantially flat cap-base with a cap-base radius, said cap-base radius defining a reservoir perimeter substantially perpendicular to said cap-height;

said at least one reservoir mounted on a rigid support substantially parallel to said reservoir perimeters;

said at least one reservoir further comprising at least one catheter connecting fluid passageway, substantially parallel to said rigid support, that connects to a catheter proximal end of a catheter;

said device configured to be completely implanted under said patient's skin;

said device configured to perform at least administering drug from said at least one reservoir, though a distal end of a catheter, to said patient's cerebrospinal fluid in said patient's cerebrospinal fluid pathway.

24. The device of claim 23, wherein said device is further configured for sampling said cerebrospinal fluid through said distal end of a catheter, and storing said sampled cerebrospinal fluid in said at least one reservoir.

* * * * *